United States Patent
Burr et al.

(10) Patent No.: US 10,752,892 B2
(45) Date of Patent: Aug. 25, 2020

(54) MULTILAYER COMPLEX, METHOD FOR MANUFACTURING SAID COMPLEX AND USE OF SAID COMPLEX

(71) Applicant: BIOMÉRIEUX, Marcy l'Etoile (FR)

(72) Inventors: Arnaud Burr, Saint Martin le Vinoux (FR); Ali Laayoun, La Frette (FR); Alain Laurent, Grenoble (FR); Raphäel Veyret, Grenoble (FR)

(73) Assignee: BIOMERIEUX, Marcy L'Etoile (FR)

( * ) Notice: Subject to any disclaimer, the term of this patent is extended or adjusted under 35 U.S.C. 154(b) by 301 days.

(21) Appl. No.: 15/537,058

(22) PCT Filed: Dec. 21, 2015

(86) PCT No.: PCT/FR2015/053673
§ 371 (c)(1),
(2) Date: Jun. 16, 2017

(87) PCT Pub. No.: WO2016/108004
PCT Pub. Date: Jul. 7, 2016

(65) Prior Publication Data
US 2017/0342400 A1    Nov. 30, 2017

(30) Foreign Application Priority Data

Dec. 30, 2014 (FR) ..................... 14 63423

(51) Int. Cl.
| | | |
|---|---|---|
| *C12N 15/10* | (2006.01) | |
| *B32B 9/00* | (2006.01) | |
| *B32B 5/08* | (2006.01) | |
| *C12Q 1/70* | (2006.01) | |

(52) U.S. Cl.
CPC ............ *C12N 15/1013* (2013.01); *B32B 5/08* (2013.01); *B32B 9/00* (2013.01); *C12Q 1/70* (2013.01)

(58) Field of Classification Search
None
See application file for complete search history.

(56) References Cited

U.S. PATENT DOCUMENTS

| 5,160,725 A | 11/1992 | Pilgrimm |
| 5,234,809 A | 8/1993 | Boom et al. |
| 6,924,033 B2 | 8/2005 | Pryor et al. |

(Continued)

FOREIGN PATENT DOCUMENTS

| EP | 1 674 571 A2 | 6/2006 |
| FR | 2 933 410 A1 | 1/2010 |

(Continued)

OTHER PUBLICATIONS

Boom et al. "Rapid and Simple Method for Purification of Nucleic Acids". Journal of Clinical Microbiology, vol. 28, p. 495-503, 1990.

(Continued)

*Primary Examiner* — Kevin M Bernatz
(74) *Attorney, Agent, or Firm* — Oliff PLC

(57) ABSTRACT

A three-layer complex including at least one magnetic compound, at least one inorganic silicate and at least one compound having an affinity for the at least one magnetic compound and/or the at least one inorganic silicate. The three-layer complex, and associated methods, may be applicable in the field of in vitro diagnostics.

26 Claims, 14 Drawing Sheets

(56) References Cited

U.S. PATENT DOCUMENTS

| | | | |
|---|---|---|---|
| 6,936,414 B2 | 8/2005 | Gundling | |
| 8,216,961 B2* | 7/2012 | Lee | B01J 21/063 502/240 |
| 8,512,946 B2* | 8/2013 | Mirkin | G01N 33/5434 435/283.1 |
| 8,563,247 B2* | 10/2013 | Yang | C12Q 1/6827 435/6.11 |
| 8,932,346 B2* | 1/2015 | Kuehling | A61L 31/08 623/1.46 |
| 2004/0067503 A1* | 4/2004 | Tan | B82Y 15/00 435/6.1 |
| 2005/0106602 A1 | 5/2005 | Akhavan-Tafti | |
| 2005/0287583 A1 | 12/2005 | Smith et al. | |
| 2006/0234251 A1* | 10/2006 | Akhavan-Tafti | C12Q 1/6806 435/6.16 |
| 2007/0087385 A1 | 4/2007 | Muller-Schulte | |
| 2007/0148651 A1 | 6/2007 | Michelsen et al. | |
| 2008/0293594 A1 | 11/2008 | Archer et al. | |
| 2009/0053512 A1* | 2/2009 | Pyun | G11B 5/712 428/336 |
| 2009/0182120 A1* | 7/2009 | Utermohlen | B82Y 5/00 530/344 |
| 2010/0009375 A1 | 1/2010 | Sherman et al. | |
| 2010/0028559 A1* | 2/2010 | Yan | H01F 1/0054 427/558 |
| 2011/0071031 A1 | 3/2011 | Khripin et al. | |
| 2011/0186524 A1 | 8/2011 | Sauer et al. | |
| 2011/0240064 A1* | 10/2011 | Wales | C09D 5/14 134/26 |
| 2012/0034670 A1* | 2/2012 | Sakai | C07F 7/1804 435/177 |
| 2014/0077121 A1* | 3/2014 | Sun | H01F 1/0054 252/62.55 |
| 2014/0243216 A1 | 8/2014 | Fabis et al. | |
| 2015/0212095 A1* | 7/2015 | Fu | G01N 33/587 435/7.92 |
| 2016/0250612 A1* | 9/2016 | Oldenburg | C01B 33/18 428/404 |
| 2017/0316487 A1* | 11/2017 | Mazed | G06Q 30/0241 |
| 2019/0336619 A1* | 11/2019 | Anderson | A61K 49/0002 |

FOREIGN PATENT DOCUMENTS

| | | |
|---|---|---|
| JP | 2013-505719 A | 2/2013 |
| WO | 2011/037692 A1 | 3/2011 |
| WO | 2014/090838 A1 | 6/2014 |

OTHER PUBLICATIONS

Berensmeier, Sonja. "Magnetic particles for the separation and purification of nucleic acids". Appl Microbiol Biotechnol, vol. 73, p. 495-504, 2006.

Magnani et al. "The Use of Magnetic Nanoparticles in the Development of New Molecular Detection Systems". Journal of Nanoscience and Nanotechnology, vol. 6, p. 1-10, 2006.

Sun et al. "Optimization of influencing factors of nucleic acid adsorption onto silica-coated magnetic particles: Application to viral nucleic acid extraction from serum". Journal of Chromatography A, vol. 1325, p. 31-39, 2014.

Basly et al. "Dendronized iron oxide nanoparticles as contrast agents for MRI". Chemical Communications, vol. 46, p. 985-987, 2010.

Daou et al. "Coupling Agent Effect on Magnetic Properties of Functionalized Magnetite-Based Nanoparticles". Chemistry of Materials, vol. 20, p. 5869-5875, 2008.

Španová et al. "Ferrite supports for isolation of DNA from complex samples and polymerase chain reaction amplification". Journal of Chromatography A, vol. 1080, 93-98, 2005.

Sugimoto et al. "Formation of Uniform Spherical Magnetite Particles by Crystallization from Ferrous Hydroxide Gels". Journal of Colloid and Interface Science, vol. 74, p. 227-243, 1980.

Maity et al. "Synthesis of magnetite nanoparticles via a solvent-free thermal decomposition route". Journal of Magnetism and Magnetic Materials, vol. 321, p. 1256-1259, 2009.

Meisen et al. "The Influence of Particle Size, Shape and Particle Size Distribution on Properties of Magnetites for the Production of Toners". Journal of Imaging Science and Technology, vol. 44, p. 508-513, 2000.

Stöber et al. "Controlled Growth of Monodisperse Silica Spheres in the Micron Size Range". Journal of Colloid and Interface Science, vol. 26, p. 62-69, 1968.

Tyagi et al. "Molecular Beacons: Probes that Fluoresce upon Hybridization". Nature Biotechnology, vol. 14, p. 303-308, 1996.

Prodělalová et al. "Isolation of genomic DNA using magnetic cobalt ferrite and silica particles". Journal of Chromatography A, vol. 1056, p. 43-48, 2004.

Lars Gunnar Sillén et al. "Stability Constants of Metal-Ion Complexes". The Chemical Society, vol. 42, p. 521, 1965.

Massart, René. "Preparation of Aqueous Magnetic Liquids in Alkaline and Acidic Media". IEEE Transactions on Magnetics, vol. 17, p. 1247-1248, 1981.

Mar. 11, 2016 International Search Report issued in International Patent Application No. PCT/FR2015/053673.

Joumaa et al. "Surface Modification of Iron Oxide Nanoparticles by a Phosphate-Based Macromonomer and Further Encapsulation into Submicrometer Polystyrene Particles by Miniemulsion Polymerization". Journal of Polymer Science, Polymer Chemistry, 2008, vol. 46, pp. 327-340.

Woo et al. "Synthesis of magnetic/silica nanoparticles with a core of magnetic clusters and their application for the immobilization of His-tagged enzymes". Journal of Materials Chemistry Royal Society of Chemistry, 2010, vol. 20, No. 3, pp. 1511-1515.

Singh et al. "Magnetic silica beads functionalized with cobalt phthalocyanine for the oxidation of mercaptans in an alkali free aqueous medium." RSC Advances 2014 Royal Society of Chemistry, 2014, vol. 4, No. 55, pp. 29124-29130.

Noori et al. "Magnetic Nanoparticles Supported Ionic Liquids Improve Firefly Luciferase Properties". Applied Biochemistry and Biotechnology, 2014, vol. 172, No. 6, pp. 3116-3127.

Zhang et al. "Fabrication and Size-Selective Bioseparation of Magnetic Silica Nanospheres with Highly Ordered Periodic Mesostructure". Advances Functional Materials, 2008, vol. 18, No. 20, pp. 3203-3212.

* cited by examiner

Three-layer complex

Solid support

1st adsorption

2nd adsorption

L 100 nm

MULTILAYER COMPLEX, METHOD FOR MANUFACTURING SAID COMPLEX AND USE OF SAID COMPLEX

The present invention relates to the field of molecular diagnostics. More specifically, it relates to solid magnetic complexes which allow the extraction and/or purification of nucleic acids (DNA and/or RNA) from biological samples or from environmental specimens, these complexes having at least three distinct layers.

The rapid development of molecular biology has made it possible to make enormous progress in diagnostics. Thus, starting from a test sample, it is possible to extract and detect nucleic acids belonging to the host or to the infectious microorganisms contained in the sample. The detection, or even the quantification, of this genetic material makes it possible to establish a diagnosis with respect to a microbial infection or to the presence of oncogenes. This is generally carried out in three steps described below:

1) The extraction of nucleic acids from complex biological samples (blood, tumor, foods, etc.) which consists in chemical or mechanical lysis of the cells in order to release the content and particularly the nucleic acids therefrom. The latter will be selectively purified so as to then be amplified if their amount is not sufficient for direct detection.
2) The amplification of the purified nucleic acids by genetic material amplification techniques: NASBA, RT PCR, PCR, etc. This step is required when the amount of nucleic acids collected from a biological sample is very low or when the test is not sufficiently sensitive for direct detection.
3) The detection of the amplified nucleic acids by techniques known as end-point, real-time, by sequencing, etc. Depending on the detection technique used, this step can enable selective quantification of the target nucleic acids sought.

For sensitive and specific detection of the nucleic acids and therefore for carrying out the most correct possible diagnosis, it appears to be essential to efficiently extract and/or isolate the nucleic acids (DNA and RNA) from the cells. This extraction and/or purification step, also known as "Sample Prep" (for sample preparation) is generally critical since all the quality of a series of events leading to the final result of the diagnostic test will ensue from this first step. Indeed, it is necessary to have a nucleic acid extraction that is as specific and efficient (in terms of amount, in terms of purity and in terms of time) as possible so as to not lose information, which can lead to an erroneous diagnosis and be fatal for a patient.

Numerous techniques have been developed to attempt to extract nucleic acids from various biological samples. The oldest methods use a multitude of steps generally consisting in enriching the cells containing the nucleic acids, in lysing these cells, in separating and removing the proteins, the membranes and other cell constituents, and in purifying the remaining nucleic acid by precipitation from organic solvents. These techniques are expensive, require a great deal of time and are often impossible to automate. Consequently, they are no longer suitable for current practices where automation is required since it makes it possible to obtain the results as quickly as possible and avoids the problems of contamination and human error, particularly in the case of sepsis ("blood infection") where the vital prognosis of a patient is on the line. The most recent nucleic acid extraction techniques use solid phases where the cells are lysed under specific reaction conditions and the nucleic acids released bind to the solid phase. It is well known in the prior art that the current nucleic acid extraction techniques very often use solid phases which are silica-coated particles. This is because silica has the property of reversibly adsorbing nucleic acids under certain salt concentration and pH conditions, which makes it a material very suitable for this purpose. These techniques are clearly described in "Rapid and simple method for purification of nucleic acids.", Boom, Journal of Clinical Microbiology, 1990 p 495 and in U.S. Pat. No. 5,234,809 by the same author.

It is also known practice to use silica-coated magnetic particles. The magnetic part of the particles usually serves to facilitate and to automate the steps of capturing, washing and eluting the nucleic acids since a simple magnet makes it possible to move the particles in the tube and to remove the supernatants for washing steps. The nucleic acid extraction yields are clearly improved by this. These techniques are well described in "Magnetic particles for the separation and purification of Nucleic acids", S. Berensmeier, Applied Microbial Biotechnology 2006 73 495-504; "The use of magnetic nanoparticles in the development of new molecular detection systems", I. J. Bruce, Journal of Nanosciences and nanotechnology and in "Optimization of influencing factors of nucleic acid adsorption onto silica-coated magnetic particles: Application to viral nucleic acid extraction from serum", Ning Sun et al., Journal of Chromatography A, 2014, 1325, 31-39.

Although these magnetic silica particles can be extremely efficient in extracting nucleic acids, their production protocol is lengthy, difficult and expensive. Indeed, the silica-coated magnetic particles used for nucleic acid extraction can sometimes be very complex to produce, particularly at the level of the silica layer which needs to be perfectly stable and controlled in terms of thickness and uniformity. The quality and the nature of this silica layer is of fundamental importance for the quality of the nucleic acids extracted and also for the reproducibility of the results from one nucleic acid extraction to another.

Thus, US 2010/0009375 A1 describes the production of magnetic particles coupled with a continuous and ultrathin layer of silica of less than 1 nm for nucleic acid extraction. This layer is, however, very difficult to measure and remains difficult to control at the level of the process. This makes the quality control of these particles very complex. If the silica layer is too thin, the nucleic acids can adsorb onto the magnetite which makes up the magnetic core without being able to be desorbed during the elution step.

US 2005/0287583 A1 and U.S. Pat. No. 6,924,033 B2 also describe the production of magnetic particles covered with a very thick layer of silica (silicon oxide/iron oxide ($SiO_2/Fe_3O_4$) ratio=40/60) which results in aggregates of which the quality and reproducibility from one batch to another can have a serious impact on the quality of the extraction. In this case likewise the production process is very complex and involves a strict control of the $SiO_2$/magnetite/$Na_2O$ reagent ratios.

Moreover, US 2011/0186524 A1 describes the production of magnetic silica particles for nucleic acid extraction, involving a step of heating at 200° C. for 7 h and the use of organic solvents; which is disadvantageous in terms of preparation time, cost and subsequent use (amplification, detection) of the nucleic acids extracted since, depending on the treatments received during the extraction, the amplification and detection yields can be affected.

In order to confront this production complexity and to avoid complex processes for controlling the thickness of the layer of coating of the magnetite, some inventors have proposed using only magnetite for carrying out nucleic acid extraction from complex media. Thus, EP 1 674 571, U.S. Pat. No. 6,936,414 and US 2007/0148651 describe the extraction of nucleic acids using particles consisting only of magnetite in an acidic medium in order to promote the interaction between the metal oxide and the nucleic acids. However, the desorption of the nucleic acids is very difficult and requires heating of the particles in a phosphate buffer in order to promote the competition with the adsorbed nucleic acids and to elute the adsorbed nucleic acids, which has a negative impact on the extraction yield. Moreover, the use of agents in the elution buffer which promote desorption, such as phosphate, can lead to a subsequent inhibition of PCR or of other techniques for amplifying the genetic material extracted. Consequently, the extraction of nucleic acids with "naked" metal oxide particles is not satisfactory.

Moreover, some inventors have modified the properties of metal oxide particles by grafting onto them various organic or inorganic compounds. Generally, said particles are stabilized by complexation with derivatives of phosphates, phosphonates, carboxylates or other organic compounds. This is described in the book "Stability constants of metal-ion complexes" by Lars Gunnar SiHen and Arthur Earl Martell published in 1971 by the Chemical Society, in U.S. Pat. No. 5,160,725, by G. Pourroy in Chem. Comm. 2010 46 985-987 or in Chem. Mater., 2008, 20 (18), pp 5869-5875. These complexes can be used as contrast agents in medical imaging, as a probe for detecting a complementary DNA strand in vivo or as biocompatible ferrofluids.

Only the works by Bohuslav Rittich in "Isolation of genomic DNA using magnetic cobalt ferrite and silica particles", B. Rittich, J. of Chromatography A, 2004, 43-48 and by David Horack in "Ferrite supports for the isolation of DNA from complex samples and polymerase chain reaction amplification", D. Horack, J. of Chromatography A, 2005, 93-98 relate to magnetic particles covered with ligands for nucleic acid extraction. On the other hand, the conditions of use are not suitable for cell lysis and nuclease denaturation since they do not use chaotropic salts for the extraction. Thus, the nucleic acid extraction and/or amplification and then detection yields are not optimal. Furthermore, nucleic acid elution problems are observed.

In the light of the disclosure of the prior art above, it appears to be clear that it was necessary to develop innovative magnetic solid supports allowing the extraction and purification of nucleic acids and which:
- are easy to synthesize and inexpensive, particularly at the level of the layer covering the magnetic compound,
- are very effective in terms of yield of capture and of elution, of extraction of the nucleic acids contained in complex biological media, in particular blood,
- make it possible to rapidly obtain highly pure nucleic acids without co-elution of inhibitors and which can, in turn, be efficiently amplified,
- are efficient for being able to capture very small amounts of nucleic acids or of biomolecules,
- make it possible to adjust the capture selectivity of double-stranded versus single-stranded nucleic acids,
- do not require the use of elution buffer that can subsequently inhibit the amplification or analysis reactions downstream of the extraction.

Thus, the subject of this invention relates to the development and production of novel solid complexes which make it possible to efficiently extract and purify nucleic acids, this being from samples, preferably complex biological samples.

Firstly, the present invention relates to a three-layer complex comprising:
- a first layer comprising at least one magnetic compound,
- a second layer at least partially covering the first layer and comprising at least one inorganic silicate compound,
- a third layer at least partially covering the second layer and comprising at least one compound having an affinity for said at least one magnetic compound and/or for said at least one inorganic silicate compound, and also the process for producing such a three-layer complex.

Secondly, the present invention also relates to the use of this three-layer complex in the purification of microorganisms and/or of biomolecules or in the extraction of biomolecules, preferably of nucleic acids, from a sample.

Thirdly, the present invention relates to the use of this three-layer complex in the detection and/or quantification of target nucleic acids, from a sample that may contain said target nucleic acids, comprising the following steps:
1. extracting the nucleic acids from a sample using this three-layer complex,
2. detecting and/or quantifying the target nucleic acids by conventional detection and/or quantification techniques.

Fourthly, the present invention relates to the use of this three-layer complex in a method of lysis of microorganisms and/or of cells, from a sample, characterized in that it consists in bringing at least one sample into contact with at least one complex according to the invention and wherein said at least one inorganic silicate compound and/or said at least one compound having an affinity for said at least one magnetic compound and/or for said at least one inorganic silicate compound comprises at least one agent of the detergent family enabling lysis.

Fifthly, the present invention relates to molecular diagnostic kits comprising at least the three-layer complex according to the invention.

The present invention thus proposes to provide three-layer complexes which are particularly useful in the molecular diagnostics field. The complexes according to the invention comprise or consist of:
- a first layer comprising at least one magnetic compound,
- a second layer at least partially covering the first layer and comprising at least one inorganic silicate compound,
- a third layer at least partially covering the second layer and comprising at least one compound having an affinity for said at least one magnetic compound and/or for said at least one inorganic silicate compound.

The term "layer" is intended to mean a thickness of material or of a substance extended so as to form a film of variable thickness. The layer may be continuous or discontinuous. The layer may also be called a coating.

The term "three-layer complex" is intended to mean a solid and compact assembly consisting of at least three physically and chemically distinct layers. In the context of a multilayer complex, the layers are superimposed, the first layer is covered with the second which closely follows the shape of the first layer, and the second layer is itself covered with the third and so on. The succession of the three layers occurs in a precise order in order to observe the properties of the complex. When the second layer is discontinuous, the third layer covers and is in direct contact with both the second layer and the first layer. On the other hand, the first layer cannot cover the second or the third layer, just as the second layer cannot cover the third layer.

Magnetic Compound

The term "magnetic compound" is intended to mean a compound capable of reacting to a magnetic field by a reaction in terms of orientation and/or of movement dependent on the strength and the orientation of said magnetic field. This force is carried out by means of the magnetic field, and is produced by moving charges or magnets. The magnetic compounds included in the three-layer complex according to the invention are chosen from metals and/or metal oxides.

Metal(s) which have magnetic properties that can be used in the three-layer complex of the present invention are iron, cobalt, nickel, steels, cast iron, and also metals which react more weakly to magnetism, such as manganese, chromium, platinum and aluminum.

The metal oxide(s) that can be used in the present invention are chosen from magnetite, maghemite and ferrites of formula $MFe_2O_4$ with M=Mn, Ni, Co, Zn etc. or any other material conventionally used in ferrites that can be doped with metal atoms other than iron.

Preferably, the magnetic compound of the complex of the invention is magnetite or maghemite, even more preferentially magnetite.

Said at least one magnetic compound of the complex of the invention may be in planar form and may form a membrane, a block. It may also have a variable shape, for example a cubic shape, the shape of a crystal, needle, cone or sphere, or the shape of a particle which can itself be spherical, multi-hedral, for example tetrahedral, octahedral, etc. The preferential shape of the magnetic compound of the three-layer complex of the invention is a particle having a size of between 1 and 500 nm, preferably between 2 and 400 nm, more preferentially between 10 and 300 nm, even more preferentially between 50 and 150 nm.

The term "particle" is intended to mean an isolated, distinct, identifiable physical structure which is insoluble in an aqueous medium or a mixture of organic and aqueous solvents or in an organic solvent and the size of which may be micrometric or nanometric. Preferably, the particle is nanometric and between 1 and 400 nm.

When said at least one magnetic compound of the three-layer complex is in the shape of a particle, then the assembly of the three-layer complex has the shape of a particle since the layer of inorganic silicate compound covering said at least one magnetic compound closely follows the shape of the latter and the same is true for the third layer with respect to the second layer.

In the case of the complex in the form of a particle, it can be said that said at least one magnetic compound forms the core of said particle since it is placed at the center thereof. However, given that the layers may cover one another only partially, the final shape of the three-layer complex is not necessarily identical to the initial shape of said at least one magnetic compound. Thus, with a magnetic compound in the shape of a particle, it is possible to obtain a three-layer complex in a random final shape. In one preferred variant of the invention, the three-layer complex has the shape of a blackberry, the magnetic compound constituting the solid core and the second layer forming a discontinuous layer formed from satellite nanospheres around the core.

The layer of magnetic compound has a micrometric or nanometric thickness.

Inorganic Silicate Compound

The term "inorganic silicate compound" is intended to mean any compound comprising silica and which is of inorganic nature. The inorganic silicate compound(s) that can be used in the three-layer complex according to the invention are silicates, magnesium, sodium, potassium, lithium or calcium silicates, talc, aluminosilicates, kaolin, bentonite, silica nanoparticles, preferably silica nanoparticles of which the size is between 0.1 and 20 nm, preferably between 1 and 20 nm, mesoporous silica nanoparticles, silica-covered magnetic nanoparticles, and also the nanoparticles mentioned above in which the silica is chemically modified with organic or inorganic groups.

The organic or inorganic groups that can modify the silica are compounds having carbon-based groups which have amine, carboxylic, thiol, alcohol, phosphonic or sulfonic acid, phosphonate and/or phosphate functions, compounds of the detergent family, such as saponins, homopolymers or copolymers, maleic anhydride polymers, N-vinylpyrrolidone, polyethylenes, propylenes and methyl vinyl ethers (AMVEs) grafted with maleic anhydride, N-vinylpyrrolidone (NVP)/N-acryloxysuccinimide (NAS), polysaccharides, amino latexes.

In one preferred variant of production of the three-layer complex according to the invention, the inorganic silicate compound is bentonite or silica nanoparticles of which the size is between 0.1 and 20 nm, even more preferentially between 1 and 20 nm.

These compounds give the best results in terms of nucleic acid extraction.

In one variant of production of the three-layer complex according to the invention, the inorganic silicate compound is made of silica nanoparticles in which the silica is modified by bonding with saponins.

These compounds give good results in terms of cell lysis which will make it possible, in combination with the three-layer complexes preferred for nucleic acid extraction, to enable an efficient and accurate molecular diagnosis.

The bonding between the first layer of the complex of the invention comprising at least one magnetic compound and the second layer comprising at least one inorganic silicate compound occurs via electrostatic or covalent bonds, giving rise to a three-dimensional structure.

In one particularly advantageous embodiment of the three-layer complex according to the invention, said at least one inorganic silicate compound is in particulate form such as a grain, a sheet, a needle, a fiber, a nanoparticle, etc., or in a form which is insoluble in an aqueous solvent, an aqueous solvent/organic solvent mixture or an organic solvent.

For example, the silica may be in the form of a grain or particle, the bentonite is generally in the form of a sheet.

The particles or forms which are insoluble in an aqueous solvent or aqueous solvent/organic solvent mixture or an organic solvent, of the inorganic silicate compound, generally have a nanometric size so as to allow good attachment of the at least one inorganic silicate compound to the layer of at least one magnetic compound. Preferably, the size of these particles or insoluble forms is between 0.1 and 20 nm, preferably between 1 and 20 nm, more preferentially between 2 and 10 nm, even more preferentially between 6 and 8 nm.

The preferred particulate form of the inorganic silicate compound is the nanoparticulate form. Thus, the first layer of the three-layer complex is at least partially coated with a second layer consisting of silica nanoparticles, preferably from 0.1 to 20 nm, more preferentially between 1 and 20 nm, even more preferentially between 2 and 10 nm and even more preferentially between 6 and 8 nm. In one preferred embodiment of the invention, the silica nanoparticles sold by the company Sigma-Aldrich, called Ludox®, are used as inorganic silicate compound; most particularly, the Ludox® SM 7 nm nanoparticles will be preferred.

The term "form which is insoluble in an aqueous solvent or aqueous solvent/organic solvent mixture or in an organic solvent" is intended to mean a structure which does not dissolve or dissolves only partially in these solvents, regardless of the temperature of the medium. They can also be referred to as insoluble form or partially insoluble form. Thus, even under aqueous conditions, this form remains well defined, in the form of a suspension, structured and identifiable. It can be observed under an electron microscope. FIG. 3 illustrates magnetite (magnetic compound) particles covered with Ludox SM 7 nm silica (inorganic silicate compound) nanoparticles, which are themselves covered with pyrophosphate (compound having an affinity for said at least one magnetic compound and/or for said at least one inorganic silicate compound). This figure thus exemplifies the complex of the invention with the inorganic silicate compound in the form which is insoluble in an aqueous solvent, in an aqueous solvent/organic solvent mixture or in an organic solvent.

The layer of inorganic silicate compound has a nanometric thickness.

Compound Having an Affinity for Said at Least One Magnetic Compound and/or for Said at Least One Inorganic Silicate Compound The term "compound having an affinity for said at least one magnetic compound and/or for said at least one inorganic silicate compound" is intended to mean a compound capable of bonding to the magnetic compound or capable of bonding to the inorganic silicate compound, whatever their respective forms. More specifically, they are molecules having an affinity for metal oxides, as described in "Stability constants of metal-ion complexes" by Lars Gunnar SiHen and Arthur Earl Martell published in 1971 by the Chemical Society. They may be of organic or inorganic nature. By way of example and non-exhaustively, mention may be made of critic acid and salts thereof, phosphate, pyrophosphate, triphosphate, polyphosphate and phosphonate ions and phosphonic acids, phosphonates or phosphonic acids coupled to organic molecules, compounds of the family of phosphoric acids, of sulfonates, compounds of the detergent family and/or compounds of the carboxylic acid family.

The organic molecules coupled to the phosphonates or phosphonic acids may be, for example, riboses, deoxyriboses, amino acids, peptides, etc.

Among the compounds of the detergent family, mention may be made of saponins, Tweens, Tritons, etc.

It is possible to envision having a three-layer complex according to the invention in which the third layer is made up of a combination of compounds having an affinity for said at least one magnetic compound and/or for said at least one inorganic silicate compound mentioned above, for example phosphate, pyrophosphate or triphosphate ions in combination with a saponin. These molecules then provide several additional properties. They can thus at the same time lyse the human cells of the test sample and capture/purify nucleic acids or biomolecules of these human cells.

It is possible to envision using various functionalizations of the second and/or third layers of the complex of the invention in order to perform selective lysis of the human cells and selective capture of bacteria, or even an enrichment of the target microorganisms and/or of the target nucleic acids or target biomolecules.

When the first layer is magnetite or maghemite, said at least one compound having an affinity for said at least one magnetic compound and/or for said at least one inorganic silicate compound is a compound having an affinity for iron.

In the preferred variants of production of the three-layer complex according to the invention, said at least one compound having an affinity for said at least one magnetic compound and/or for said at least one inorganic silicate compound consists of monophosphates, pyrophosphates, triphosphates, citric acid or salts thereof, and/or saponin.

The bonding between the second layer of the complex of the invention comprising at least one inorganic silicate compound and the third layer comprising at least one compound having an affinity for said at least one magnetic compound and/or for said at least one inorganic silicate compound occurs via electrostatic or covalent or coordination bonds giving rise to a three-dimensional structure.

In the embodiment wherein the second layer of the complex according to the invention consists of particles or nanoparticles, preferably nanoparticles of silica, interstices can occur between said particles or nanoparticles, and the third layer comprising at least one compound having an affinity for at least one magnetic compound has easier and better adhesion to the first layer since some metal and/or metal oxide atoms of the first layer are available and more accessible for forming a reaction or producing a bond.

The layer of compound having an affinity for the at least one magnetic compound and/or the at least one inorganic silicate compound has a thickness which is nanometric or smaller.

In one particular embodiment, the three-layer complex according to the invention and as defined above also comprises a solid support under all or part of the first layer made up of the at least one magnetic compound.

The term "solid support" is intended to mean any support capable of supporting the layer of at least one magnetic material. It can be at least one flat support, one hollow support, one round piece, one needle, one membrane, one block, one sheet, one cone, one tube, one bead, one particle, etc. The support is preferably a bead or a particle.

The bonding of the support with the first layer of at least one magnetic compound occurs via electrostatic bonds, by covalent bonds or by any other physical or chemical means. For example, it is possible to use an adhesive for attaching said at least one magnetic compound to the support or an intermediate substance capable of maintaining the bond between the solid support and the magnetic compound, for instance a protein, a polymer, a hydrophilic or hydrophobic polymer, a polydopamine, etc.

In one particular embodiment, the three-layer complex as defined above, with or without support, is in the form of a particle and said third layer comprising at least one compound having an affinity for said at least one magnetic compound and/or for said at least one inorganic silicate compound lies at the exterior of the particle. In a way, the core of the particle is made up of:
1) the support which is in turn coated with the three-layer complex of the invention with the first layer in contact with the support, the second layer in contact with the first layer and the third layer in contact with the second layer or the first layer, when the second layer is discontinuous, and constituting the external film-coating of the final particle, or
2) said at least one magnetic compound coated with the second and third layers, the third layer constituting the external shell of the final particle.

In this production variant, the preferred form is a three-layer complex having the form of a particle of which the first layer constitutes the core of said particle and has a size of between 2 and 400 nm, preferably between 50 and 100 nm.

The most particularly preferred forms of the complex according to the invention are complexes comprising magnetite between 50 nm and 100 nm (first layer), nanoparticles of silica (most preferentially Ludox SM 7 nm) or of bentonite (second layer) and monophosphate, pyrophosphate, triphosphate ions (third layer).

In the complex according to the invention, when it is in the form of a particle, the weight-to-weight (or w/w) ratio between said at least one inorganic silicate compound and said at least one magnetic compound represents between 0.1% and 60%, preferably between 1% and 50%, more preferentially between 3% and 35%, even more preferentially between 4% and 10%.

In the preferential variants of implementation of the invention, the weight/weight ratio of inorganic silicate compound to magnetic compound is higher when the inorganic silicate compound is in the form of a sheet, for instance bentonite, than when it is in the form of nanoparticles. For example, when the magnetite particle is covered with bentonite, the bentonite/magnetite ratio is between 25% and 55%, whereas if it is covered with Ludox nanoparticles, the Ludox/magnetite ratio is between 1% and 10%.

In the same context, when the complex according to the invention is in the form of a particle, the molar ratio of said at least one magnetic compound (preferably iron)/at least one compound having an affinity for said at least one inorganic silicate compound and/or at least one magnetic compound is between 0.1% and 15%, preferably between 0.1% and 10%, more preferentially between 5% and 10% and even more preferentially between 6% and 9%.

Production Method

The three-layer complex according to the invention is produced by production methods that are easy to carry out and highly reproducible. This makes it possible to have a reliability in the performance levels of the complex produced and also uniformity, or at least very few variations, from one batch of complex produced to another.

Furthermore, the methods for producing the complex of the invention that are used are inexpensive and certain production variants are very fast.

In order to carry out the methods for producing the complex according to the invention, the methods for supplying the various constituents of the complex of the invention should first of all be described.

Supply of Carrier Magnetic Compound

Said at least one magnetic compound is either found naturally, or it is synthesized according to conventional protocols described in the literature or by coprecipitation as described by R. Massart (IEEE Trans. Magn. 1981, 17, p 1247-1248.), or by partial oxidation of metal salts as described by T. Sugimoto and E. Matjevic (Journal of Colloids and Interface Science, 1980, 74, P 227-243), or by decomposition of organometallic precursors as described by Maity (Journal of Magnetic Materials 321 1256 (2009)). The advantage of these techniques is that it is possible to easily incorporate other metal atoms, such as cobalt, manganese, zinc, etc., so as to obtain ferrites which can also be used as magnetic compound as described above in the complex of the invention.

Alternatively and preferably, said at least one magnetic compound can be purchased commercially. This is the case in particular with the metal oxide nanoparticles which can be purchased from suppliers of magnetic ink pigments as described in *The Journal of Imaging Science and Technology November/December* 2000, vol. 44, no. 6; p. 508-513 *"The Influence of Particle Size, Shape and Particle Size Distribution on Properties of Magnetites for the Production of Toners"*.

Supply of Inorganic Silicate Compound

Said at least one inorganic silicate compound as described above, for example of the magnesium or sodium trisilicate, bentonite, kaolin, talc, etc., type, can be easily purchased from suppliers of chemical products such as Sigma-Aldrich (St Louis, USA). Moreover, many conventional protocols known to those skilled in the art describe how to obtain these inorganic silicate compounds. For example, the inorganic silicate nanoparticles used in the preferred embodiment of the invention can be synthesized according to conventional protocols for condensation of tetraethoxysilane (TEOS) in an aqueous and alkaline medium, which are described in the literature by W. Stöber (Journal of Colloids and Interface Science 1968, 26, p 62-69). Alternatively, the silicate-comprising nanoparticles can be obtained from suppliers of chemical products such as the company Sigma-Aldrich (St Louis, USA) supplying for example the particles of the Ludox range or equivalents thereof, or such as the company NanoH (Lyons, France). It is possible and easy to introduce functional groups such as amino, phosphonate, azido, alkyne, etc., groups under these inorganic silicate compounds (preferably the nanoparticles) by co-condensation of the corresponding silanes with TEOS so as to increase the force of interaction with the at least one magnetic compound (for example phosphonate nanoparticles).

Supply of Compound Having an Affinity for Said at Least One Magnetic Compound and/or for Said at Least One Inorganic Silicate Compound These compounds having an affinity for said at least one magnetic compound and/or for said at least one inorganic silicate compound are generally products that are readily available from suppliers of chemical products. If not, they are easily prepared chemically by conventional methods known to those skilled in the art.

The present invention relates to a method for preparing at least one three-layer complex as defined above, characterized in that it comprises at least the following steps:

a0) optionally bringing a support as defined above into contact with at least one magnetic compound as defined above such that the at least one magnetic compound attaches or bonds to the support, a) bringing the result of step a0) or at least one magnetic compound as defined above into contact with at least one inorganic silicate compound as defined above, such that an electrostatic interaction and/or a covalent bond and/or a coordination bond occurs between said at least one magnetic compound and said at least one inorganic silicate compound and such that the layer of said at least one inorganic silicate compound at least partially covers the layer of said at least one magnetic compound, b) bringing the complex obtained in step a) (two-layer complex consisting of said at least one magnetic compound/at least one inorganic silicate compound, with or without support), into contact with at least one compound having an affinity for said at least one magnetic compound and/or for said at least one inorganic silicate compound as defined above, preferably in an aqueous medium, such that said at least one compound having an affinity for said at least one magnetic compound and/or for said at least one inorganic silicate compound adheres and positions itself above the layer of said at least one inorganic silicate compound of the two-layer complex, with or without support, or above the magnetic compound when the layer of the at least one inorganic silicate compound is discontinuous.

Generally, one or more washes in water or in an aqueous medium are carried out after each of the steps of producing the complex according to the invention, preferably after step a) and b).

The bonding of the second layer to the first layer takes place by adsorption and by electrostatic bonding and/or by covalent bonding and/or a coordination bond. The same is true for the bonding of the third layer to the second layer.

In one implementation variant, the complex comprises a support to which the complex is attached or bonded. The support is as described above. In this case, the method for producing the complex on the support can be carried out in several ways:

- either the support is brought into contact with the at least one magnetic material such that an interaction occurs between the two materials, either by electrostatic bonds or by covalent bonding or by coordination bonding, and then the second layer is added to the first layer attached to the support, the second layer attaching to the first layer and not to the support, then the third layer is added to the two-layer complex attached to the support,
- or the support is brought into contact with a two-layer complex consisting of the first layer bonded to the second layer, the support then attaching to the first layer of the two-layer complex in the same way as that which is described above, then the third layer is added to the two-layer complex attached to the support,
- or the support is brought into contact with the three-layer complex already formed and it attaches to the first layer of the three-layer complex in the same way as that which is described above.

The support has a millimetric to micrometric thickness.

Use may also be made of a material which makes it possible to physically or chemically attach the first layer of the complex to the support. It may be an adhesive or any other compound capable of performing this function, namely an intermediate substance capable of maintaining the bond between the solid support and the magnetic compound, for instance a protein, a polymer, a hydrophilic or hydrophobic polymer, a polydopamine, etc.

In one preferred variant of implementation of the invention, the final complex is in the form of a particle comprising a core of at least one magnetic compound, which is at least partially covered with two layers: a layer of at least one inorganic silicate compound and a layer of compound having an affinity for said at least one magnetic compound and/or for said at least one inorganic silicate compound, this final layer being located on the outside of the complex.

Thus, the method of preparation of the preferred embodiment of the invention comprises at least the following steps:

a) bringing at least one magnetic compound as defined above into contact with at least one inorganic silicate compound as defined above, said inorganic silicate compound already being in particulate form, nanoparticulate form or insoluble form, such that an electrostatic interaction and/or a covalent bond and/or a coordination bond occurs between said at least two compounds and that the particles or insoluble forms at least partially cover the particle of at least one magnetic compound constituting the core, b) bringing the coated particle obtained at the end of step a) into contact with at least one compound having an affinity for said at least one magnetic compound and/or for said at least one inorganic silicate compound as defined above, preferably in an aqueous medium, such that an electrostatic interaction and/or a covalent bond and/or a coordination bond occurs between said at least one compound having an affinity for said at least one inorganic silicate compound and/or said at least one magnetic compound and said at least one inorganic silicate compound of the two-layer complex obtained at the end of step a) or said at least one magnetic compound of the two-layer complex obtained at the end of step a) and that said at least one compound having an affinity for said at least one inorganic silicate compound and/or said at least one magnetic compound adheres to the surface of said at least one inorganic silicate compound or to the core of the final particle.

Preferably, the interaction between said at least one magnetic compound and said at least one inorganic silicate compound is noncovalent, likewise for the interaction between said at least one compound having an affinity for said at least one inorganic silicate compound and/or said at least one magnetic compound and said at least one inorganic silicate compound or said at least one magnetic compound.

Generally, one or more washes in water or in an aqueous medium are carried out after each of the steps of producing the complex according to the invention.

The contact between said at least one magnetic compound and said at least one inorganic silicate compound is generally carried out at a pH of between 2 and 7, preferably between 3 and 6, most preferentially between 3 and 4. In general, the coating of the first layer of said at least one magnetic material is promoted by opposite electrostatic interactions. Thus, the coating should be carried out in a pH range where the at least one inorganic silicate compound and said at least one magnetic compound have opposite surface charges as described in U.S. Pat. No. 4,280,918.

In the preferred embodiment of the complex of the invention, magnetite is used as magnetic compound and silica is used as inorganic silicate compound. The isoelectric point of magnetite is at 6.8 and that of silica is at around 2; the coating of the magnetite by the silica should be carried out at a pH of between 2 and 6.8, preferably at a pH of 3.5.

For the method of producing the complex, the temperatures used are between 15° C. and 65° C., preferably between 20° C. and 60° C. used.

The preferred embodiment of the invention is very easy and fast to synthesize since it uses commercially available or easily synthesizable compounds.

Thus, in a first step, said at least one magnetic compound (preferably the magnetite particles) is incubated at between pH 3 and 6 with said at least one inorganic silicate compound (preferably the Ludox inorganic silicate nanoparticles) in order to give a positive charge to said at least one magnetic compound and a negative charge to said at least one inorganic silicate compound. In this way, the two types of compounds (in the form of particles in the preferentially chosen form of the invention) bond to one another very solidly by forming a three-dimensional structure (in the shape of a blackberry in the case of the use of magnetite and of the Ludox particles).

In general, the temperature used at this first step is ambient temperature, but the temperature can vary between 20° C. and 60° C.

The composite complexes obtained, that is to say the two-layer complexes (or in the preferential form, the Ludox-covered particles), are then washed by magnetization or by any appropriate known technique making it possible to obtain the same function.

In a second step, at least one compound having an affinity for said at least one magnetic compound and/or for said at least one inorganic silicate compound is coated onto the two-layer complex consisting of at least one magnetic compound covered with at least one inorganic silicate compound. This is carried out by incubation of said two-layer complex with said at least one compound having an affinity for said at least one magnetic compound and/or for said at least one inorganic silicate compound in an aqueous medium for 30 seconds to 24 h, preferably 2 h, at controlled pH and controlled temperature.

In general, the temperature used at this step is ambient temperature, but the temperature can vary between 20° C. and −60° C.

The three-layer complex is again washed by magnetization or any other known technique having the same function, and it can then be taken up in water in order to determine the concentration by measuring the solids.

The washes are generally carried out in water or at least in an aqueous medium.

This method of coating the layer of at least one magnetic compound with at least one inorganic silicate compound and in particular with forms which are insoluble in an aqueous solvent (inorganic silicate particles) is described in U.S. Pat. No. 4,280,918.

In an original, rapid and reliable manner, one of the methods of producing the complex according to the invention that is particularly advantageous is to use at least one magnetic compound, preferably at least one magnetite or maghemite particle, and to deposit on the latter or to at least partially cover the latter with at least one inorganic silicate compound, preferably an inorganic silicate compound which is insoluble in nature and already structured, such as particles (for example silica nanoparticles) or sheets (for example bentonite). For example, as inorganic silicate compound, use will preferably be made of silica nanoparticles between 0.1 and 20 nm, more preferentially between 1 nm and 20 nm and even more preferentially Ludox® SM 7 nm particles. When these types of compounds are used, the production of the complex is simplified because these inorganic silicate compounds are commercially available. Furthermore, their size is perfectly controlled and thus the production of the complex is very reproducible and standardizable. In this variant of production of the complex, simple adsorption of said at least one inorganic silicate compound onto said at least one magnetic compound under good pH conditions is thus sufficient to generate a layer of silica of the desired thickness, controlled and regulated by the size of the inorganic silicate nanoparticles chosen. Subsequently, during the coating with the third layer, the gaps between the nanoparticles of inorganic silicate material are filled with said at least one compound having an affinity for said at least one magnetic compound and/or for said at least one inorganic silicate compound. This is generally the case when said at least one compound forming the third layer preferentially has an affinity for said at least one magnetic compound. When the compound forming the third layer of the complex has an affinity for said at least one inorganic silicate compound which is stronger than for the magnetic compound, it is not essential for there to be gaps in the second layer of the complex.

It should be noted that this embodiment of the complex involves an increase in the developed surface area of the complex (or specific surface area) and thus an increase in the nucleic acid extraction/purification capacity.

Furthermore, by judiciously choosing inorganic silicate particles which have notable functions (amines, carboxylic acids, etc.), it is possible to easily functionalize the magnetic compound with these functions without the need to involve processes, which are complicated to control, of condensation of silanes on magnetite in the presence of organic solvent(s).

In order to provide very good nucleic extraction and/or purification capture capacities, it is preferable for said at least one magnetic compound to be entirely coated with said at least one inorganic silicate compound.

It can thus be understood that one of the advantages of the three-layer complex according to the invention lies in the simplicity of use and production thereof. However, the advantages of this complex are not limited to its production, the advantages of its use are many. Indeed, surprisingly, it has been noted that the complex according to the invention offers notable and particularly advantageous properties in the capture and elution of nucleic acids and in particular in complex media or biological samples.

The three-layer complexes of the invention have been evaluated for their capacity to extract nucleic acids from cells or from bacteria contained in a complex medium or sample such as blood.

The term "sample" is intended to mean a sample having various origins, such as swabs of food, environmental, human, veterinary or cosmetic origin.

Among the samples of food origin, mention may be made, nonexhaustively, of a sample of milk products (yogurts, cheeses, etc.), of meat, of fish, of eggs, of fruit, of vegetables, of beverages (milk, fruit juice, soda, etc.). Of course, these samples of food origin may also come from sauces or more elaborate dishes or non-transformed or partially transformed raw materials. A food sample may also be derived from an animal feed, such as oil cakes or animal meals. All these samples, if they are not liquid, are pretreated so as to be in liquid form.

As previously indicated, the sample may be of environmental origin and may consist, for example, of a surface sampling, a water sampling, etc.

The sample may also consist of a biological sample, of human or animal origin, which may correspond to samplings of biological fluid (urine, total blood or derivatives such as serum or plasma, sputum or saliva, pus, cerebrospinal fluid, etc.), of stools (for example choleraic diarrhea), nose, throat, skin, wound, organ, tissue or isolated-cell samplings, swab samples, bronchoalveola samplings or lavages, or biopsies. This list is obviously not exhaustive.

In general, the term "sample" refers to a portion or an amount, more particularly a small portion or a small amount, taken from one or more entities for analytical purposes. This sample can optionally have undergone a pretreatment, involving for example mixing, diluting or else milling steps, in particular if the starting entity is in the solid state.

The sample analyzed is, in general, capable of—or suspected of—containing at least one biomolecule representative of the presence of microorganisms or of a disease to be detected, characterized or monitored.

The term "biomolecule" is intended to mean a compound or a chemical entity that may be a nucleic acid (DNA or RNA of any type, genomic DNA, complementary DNA, messenger RNA, complementary RNA, transfer RNA, mitochondrial RNA, chloroplast DNA, ribosomal RNA, plasmid DNA, viral DNA or RNA, microRNA, snoRNA, siRNA, iRNA, in single-stranded or double-stranded form) or a protein.

The term "microorganism" is intended to mean all or part of a bacterium, of a fungus, of a yeast or of a virus.

Thus, the present invention also relates to a method for purifying microorganisms and/or biomolecules or for extracting biomolecules, preferably nucleic acids, from a sample, preferably a biological sample, in which at least one complex as defined above is used.

The term "extraction" is intended to mean a technique which makes it possible to isolate biomolecules from a sample whatever it is, for example the isolation of DNA or RNA from eukaryotic cells, prokaryotic cells, human cells or animal cells, from microorganisms or from a tissue. Thus, for the purposes of the invention, the extraction includes the lysis and purification of biomolecules.

The purification itself comprises the adsorption or capture, the washing and the elution of the biomolecules and/or of the microorganisms. The capture consists in adsorbing the biomolecules and/or microorganisms onto the complex and the elution to the desorption or release of the latter from the complex according to the invention. When reference is made to the purification of microorganisms, there is no lysis of the latter; it may then be a question of an enrichment in microorganisms.

Preferably, the tests of the complex are carried under chaotropic conditions which are conditions where the three-dimensional structures of the biological micromolecules, such as the proteins, DNA or RNA, are denatured. Chaotropic agents interfere with weak (noncovalent) intramolecular interactions, such as hydrogen bonds, van der Waals forces and hydrophobic forces. Among the chaotropic agents, mention may be made of urea, guanidine salts, such as guanidinium chloride or thiocyanate, and lithium perchlorate. They are generally used in a concentration ranging from 1 to 6 M, in particular for GuSCN and GuHCl.

Generally, a detergent is also added, which assists with the lysis of the cells, said detergent possibly being chosen from Tween, tritons, SDS and other detergents commonly used at concentrations of between 0.05% and 5% by weight or by volume relative to the lysis buffer.

Thus, the proteins capable of denaturing or damaging nucleic acids, such as nucleases, are inhibited or destroyed under the chaotropic conditions and this provides the most favorable conditions for efficiently extracting nucleic acids. Preferably, for the capture of the nucleic acids in the present invention, guanidinium chloride or guanidinium thiocyanate and/or hydrochloric acid (HCl) in a medium buffered at pH 7 and a detergent (preferably triton X100), are used.

The complex according to the invention offers highly effective properties in the purification and/or extraction of biomolecules and/or microorganisms and in particular in the extraction of the nucleic acids.

The good properties of nucleic acid capture via magnetic particles coated with silica are widely known. It is shown in the present application that adding a compound having a strong affinity for said at least one magnetic compound to a particle of magnetic compound affects DNA capture. On the other hand and very surprisingly, in the complex according to the invention in which there is a magnetic compound covered with at least one inorganic silicate compound, itself covered with at least one compound having an affinity for said at least said one inorganic silicate compound and/or for the at least one magnetic compound, that is to say a combination of the two types of particles already known and described above, the capture of the nucleic acids and particularly of the DNA is not at all affected, it is even potentiated. This synergistic effect was absolutely not foreseeable. It was instead foreseeable that said at least one compound having an affinity for said at least one inorganic silicate compound and/or for the at least one magnetic compound would totally displace the coating of inorganic silicate compound and cause the DNA extraction yield to drop. Likewise, it could not be envisioned from the types of particles previously described that the three-layer complex would improve the RNA elution capacities and would thus offer DNA and RNA nucleic acid purification and extraction properties that are clearly improved compared with the prior art. The examples very clearly illustrate this phenomena and although the examples are limited to a few magnetic compounds, inorganic silicate compounds and compounds having an affinity for said at least one inorganic silicate compound and/or for said at least one magnetic compound, it is entirely possible for those skilled in the art to generalize the effects obtained to the various possible and envisionable combinations of these three compounds listed above for forming a three-layer complex according to the invention.

As has been specified above, the particularly preferred form of inorganic silicate compound is made up of the silica nanoparticles of between 0.1 and 20 nm, more preferentially between 1 and 20 nm. It should be noted that the smaller the size of the inorganic silicate compound nanoparticles bonded to the first layer, which is the magnetic layer, of the complex of the invention, the greater and more efficient the extraction of the nucleic acids with the complexes according to the invention. In a way, the particle size influences the nucleic acid extraction yield and the greater the specific surface area of the inorganic silicate compound nanoparticles, the better the nucleic acid extraction: a complex having magnetite covered with Ludox® HS 40 inorganic silicate compound nanoparticles will capture fewer nucleic acids than a complex having magnetite covered with Ludox® SM 7 nm inorganic silicate compound nanoparticles.

In order to obtain good results in the purification of microorganisms and/or biomolecules or the extraction of biomolecules, in particular of nucleic acids, the weight-by-weight ratios of inorganic silicate compound/magnetic compound are between 0.1% and 60%, preferably between 0.5% and 30%, more preferentially between 1% and 20%, even more preferentially between 2% and 15%, most particularly preferably between 3% and 10%.

In order to obtain good results in the purification of microorganisms and/or biomolecules or the extraction of biomolecules, in particular of nucleic acids, the weight-by-weight ratios of magnetic compound/compound having an affinity for said at least one magnetic compound and/or for said at least one inorganic silicate compound are between 0.1% and 20%, preferably between 0.1% and 10%, more preferentially between 4% and 8%.

In another of its aspects, the present invention relates to a method for detecting and/or quantifying biomolecules, in particular target nucleic acids, from a sample that may contain said target nucleic acids, comprising the following steps:
1) extracting the nucleic acids from a sample by carrying out the method as described above,
2) detecting and/or quantifying the target nucleic acids by conventional detection and/or quantification techniques.

Indeed, once the biomolecules have been extracted with the complex according to the invention, it is advantageous to detect the target nucleic acids, or even to quantify them, in order to provide a precise diagnosis. These target nucleic acids are those suspected or capable of being present in the sample tested.

The conventional detection methods that can be used are all those that are widely known by those skilled in the art. For example, mention may be made, nonexhaustively, of radioactive labelings; cold labelings: colorimetry, fluorescence, chemiluminescence; molecular hybridizations; Southern Blots; Northern Blots; Dot Blots or in situ hybridization. Preferentially, detection with a detection probe is used. The term "detection probe" or "probe" is intended to mean a nucleic sequence of a nucleotide chain of four bases of different types chosen from the group of adenine, thymine, guanine, uracil and cytosine, which is capable of hybridizing specifically on an amplicon, and comprising at least one label. The probe may be a probe of rounded shaped (called O-probe, see patent application by the applicant FR08/54549 filed on Jul. 4, 2008), a Molecular Beacon, a Taqman® probe or a FRET probe. These latter three types of probe are well known to those skilled in the art. These probes can optionally consist totally or partially of modified nucleotides. Each probe comprises a label and optionally a quencher. Among these probes, use is preferentially made of probes which emit a fluorescence when they hybridize to the complementary sequence, probes described by Tyagi & Kramer (Nature Biotech, 1996, 14:303-308), commonly known as "molecular beacons" or commercial kits, for instance kits of the R-Gene® range from Argene (bio-Mérieux, Verniolle, France). It is possible to carry out the detection in real time or at the end of the reaction.

The quantification methods used are the standard quantification methods conventionally used by those skilled in the art. For example, it is possible to use quantification kits of the R-Gene® range from Argene (bioMérieux, Verniolle, France). These methods conventionally involve ranges of quantification standards (QSs) which make it possible to evaluate the actual amount of a given nucleic acid or of nucleic acids in the sample tested.

In one implementation variant, the present invention relates to a method for detecting and/or quantifying target nucleic acids, as described above, wherein, between the step of extracting the nucleic acids and the step of detecting the nucleic acids, there is a step of eluting the nucleic acids from the complex used in the extraction step and/or a step of amplifying the nucleic acids by conventional techniques.

The elution step is generally carried out using a solution at slightly alkaline pH and low ionic strength at a temperature of between 50° C. and 70° C. In general, commercial products are preferably used, such as the products of the NucliSENS easyMAG extraction range (bioMérieux, France). These conditions are conventional conditions for preserving the integrity of nucleic acids and are standard conditions.

The term "amplification" or "amplification reaction" is intended to mean any nucleic acid amplification technique well known by those skilled in the art.

The amplification step is generally carried out because the amount of nucleic acids to be detected and/or quantified is very low and it is necessary to involve a phase of amplification of the latter in order to detect them and/or to quantify them in order to give a precise diagnosis. Without an amplification phase, it is entirely possible to obtain erroneous results leading to the conclusion that a target nucleic acid is absent in a sample, whereas in reality it is present in the latter but in such a small amount that the techniques used do not make it possible to detect it. Thus, numerous amplification methods can be used, such as PCR, RT-PCR, LCR, RCR, 3SR, RCA, NASBA, TMA, SDA or any of the nucleic acid amplification techniques known to those skilled in the art.

The target nucleic acid detection and/or amplification tests carried out with the complexes according to the invention give excellent results.

In another of its aspects, the present invention relates to a method for lysing microorganisms and/or cells and/or tissues, from a sample, characterized in that it consists in bringing at least one sample into contact with at least one three-layer complex as described above and in which said at least one inorganic silicate compound and/or said at least one compound having an affinity for said at least one magnetic compound and/or for said at least one inorganic silicate compound comprises at least one agent of the detergent family enabling lysis.

In certain analytical situations, it may be advantageous to lyse cells, the cells of a tissue and/or microorganisms in a targeted manner. Thus, the use of this complex may be advantageous when it is a question of targeting a certain cell type or microorganism type. For example, in the context of sepsis, it may be necessary to lyse, in a targeted and selective manner, the membranes and the nucleic acid cells of the human blood cells present in large amount in a sample. This can be carried out with saponin which penetrates and weakens the membranes and the envelopes containing cholesterol. It may be necessary to perform this selective lysis with a view to be able to select and extract the pathogenic microorganisms present in very small amounts in the sample tested. After lysis of these microorganisms represented in very low number, it will be possible to purify their nucleic acids and to selectively amplify them with very high sensitivity despite the fact that they are present in a very small amount in the initial sample. The three-layer complex according to the invention could assist in this sense. As has been described above, the compounds constituting the second and/or the third layer of the complex of the invention can be functionalized with compounds of the detergent family, such as saponins for example. Thus, these complexes thus functionalized can have a role in the selective lysis of human cells. Thus, the three-layer complex could be used to perform a first step of selective lysis and capture of the nontargeted nucleic acids and to in a way facilitate a step of targeted enrichment of microorganisms present in the sample but not captured by the complexes of the invention.

It can also be envisioned to have a three-layer complex according to the invention of which said at least one inorganic silicate compound and/or said at least one compound having an affinity for said at least one magnetic compound and/or for said at least one inorganic silicate compound are functionalized in different and complementary ways and make it possible to capture and/or lyse various types of biomolecules and/or microorganisms.

In the preferred embodiment of the invention according to this method, said at least one inorganic silicate compound comprises silica nanoparticles between 0.1 nm and 20 nm, more preferentially between 1 nm and 20 nm, the silica of which is bonded with saponins and/or the compound having an affinity for said at least one magnetic compound and/or for said at least one inorganic silicate compound is coupled to at least one saponin. It is possible for the functionalization not to be complete, that is to say that the compounds thus functionalized may only partially cover said at least one magnetic compound.

All the inorganic silicate compounds and all the compounds having an affinity for the at least one magnetic compound and/or for the inorganic silicate compound listed above are "functionalizable" with a detergent of saponin type. In one preferred embodiment for the use of selective cell or microorganism lysis, the inorganic silicate compound is a Ludox® 7 nm silica nanoparticle and the compound having an affinity for the at least one magnetic compound and/or the at least one inorganic silicate compound is chosen from dopamine and derivatives thereof, catechols and derivatives thereof, phosphonic acids, phosphonates, phosphates and the compounds of the carboxylic acid family (preferably citric acid and salts thereof), preferably coupled to at least one saponin.

Finally, in a last aspect, the present invention relates to a molecular diagnostic kit comprising at least one three-layer complex according to the invention defined above.

The latter can also include reagents which enable the specific amplification of the nucleic acids that may be or that are suspected of being contained in the sample to be tested, and/or reagents for detecting and/or quantifying the nucleic acids that may be or that are suspected of being contained in the sample to be tested.

These kits will make it possible to carry out the various extraction and/or detection and/or quantification methods described above.

The examples and figures attached hereto represent particular embodiments of the invention and cannot be considered to limit the scope of the present invention.

FIGURES

The various figures assist with the understanding of the invention and illustrate the results and performance obtained with the complex according to the invention.

FIG. 1 is a diagram of the complex according to the invention in one possible embodiment, the hatching representing the solid support, the stars representing the at least one magnetic compound, the circles representing said at least one inorganic silicate compound and the letter L representing said at least one compound having an affinity for said at least one magnetic compound and/or for said at least one inorganic silicate compound.

FIG. 2 is a diagram of the formation of the complex according to the invention in one preferred embodiment.

FIG. 3 corresponds to an electron microscopy image of complexes according to the invention: magnetite particles virtually entirely covered with Ludox® SM 7 nm inorganic silicate nanoparticles and pyrophosphate (invisible on the figure).

FIG. 4 represents the DNA capture yield (black) and elution yield (squared) for magnetite particles covered with inorganic silicate compounds.

FSC 419 corresponds to the results obtained with 100 nm magnetite particles;

AL1001 corresponds to the results obtained with 100 nm magnetite particles covered with Ludox® 6% (weight/weight) at pH 3.5;

AL1018 corresponds to the results obtained with 100 nm magnetite particles covered with $MgSiO_4$ 50% (weight/weight) at pH 3.5;

AL 1024 corresponds to the results obtained with magnetite particles covered with $NaSiO_4$ 50% (weight/weight) at pH 3.5;

AL 1014 corresponds to the results obtained with magnetite particles covered with bentonite 30% (weight/weight) at pH 3.5.

AB 930 corresponds to magnetite particles alone;

KE54a corresponds to the results obtained with magnetite particles covered with phosphate ions at 6 mol %. The term "mol %" in the figures and examples is intended to mean the molar ratio of iron/compound having an affinity for the inorganic silicate compound and/or the magnetic compound (that can also be referred to as ligand);

KE220 corresponds to the results obtained with magnetite particles covered with pyrophosphate ions at 6 mol %;

KE351 corresponds to the results obtained with magnetite particles covered with triphosphate ions at 6 mol %;

KE225 corresponds to the results obtained with magnetite particles covered with HEEEPA ((2-(2-(2-hydroxyethoxy)ethoxy)ethyl)phosphonic acid) (Sikemia, Montpellier, France) at 10 mol %;

KE231 corresponds to the results obtained with magnetite particles covered with NTPA (nitrilotris(methylene) triphosphonic acid) (Acros, Geel, Belgium) at 0.1 mol %.

Figure 7A:
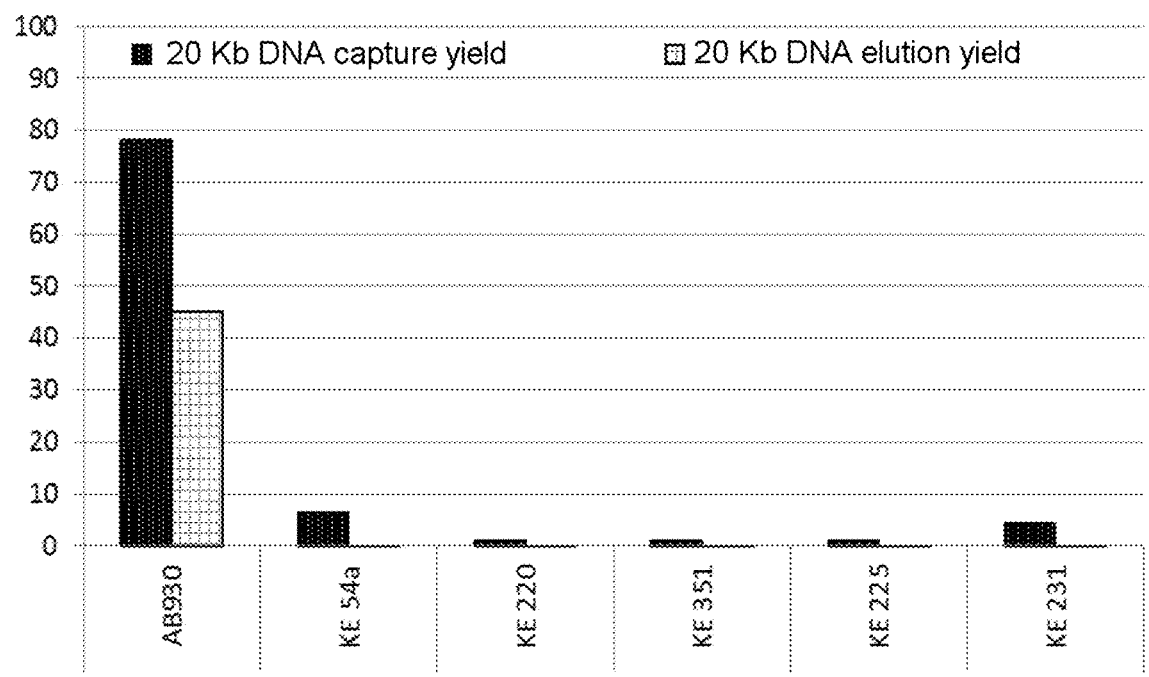
FIG. 7A represents the DNA and RNA capture yield (black) yield and elution yield (squared) for magnetite particles coated with a compound having an affinity for said at least one magnetic compound and/or for said at least one inorganic silicate compound.
Figure 7B:
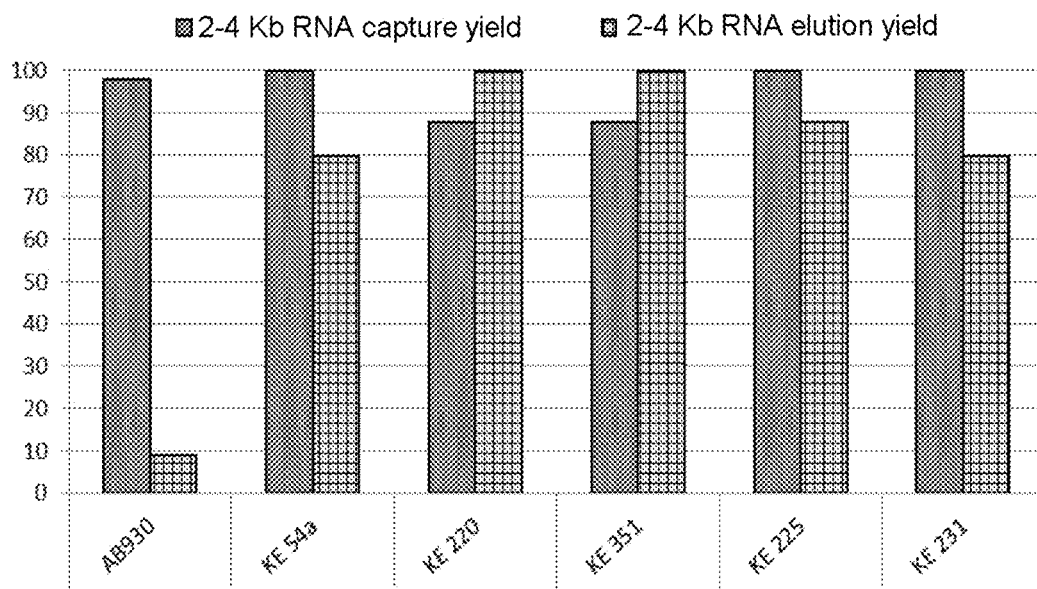

FIG. 7B represents the RNA capture yield (gray) and elution yield (squared) for the same particles as those of FIG. 7A.

Figure 8:
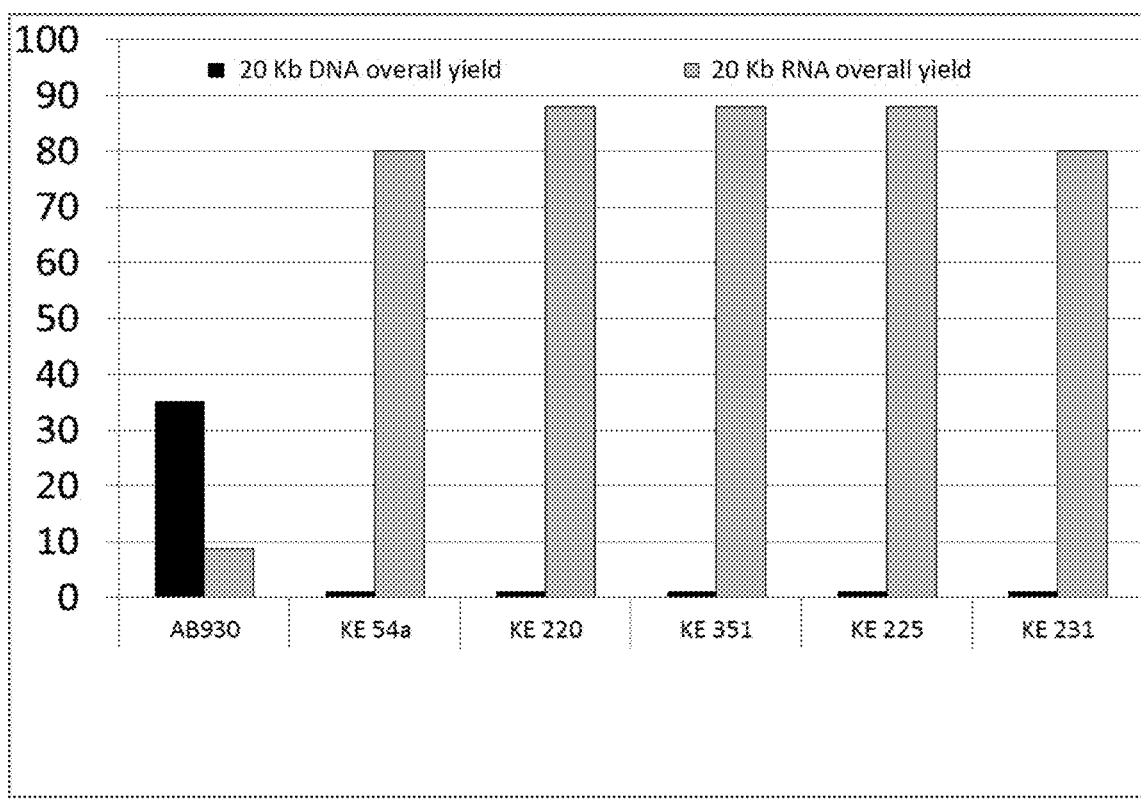

FIG. 8 represents the overall DNA extraction (black) and RNA extraction (gray) yield for particles of FIGS. 7A and 7B.

Figure 9:
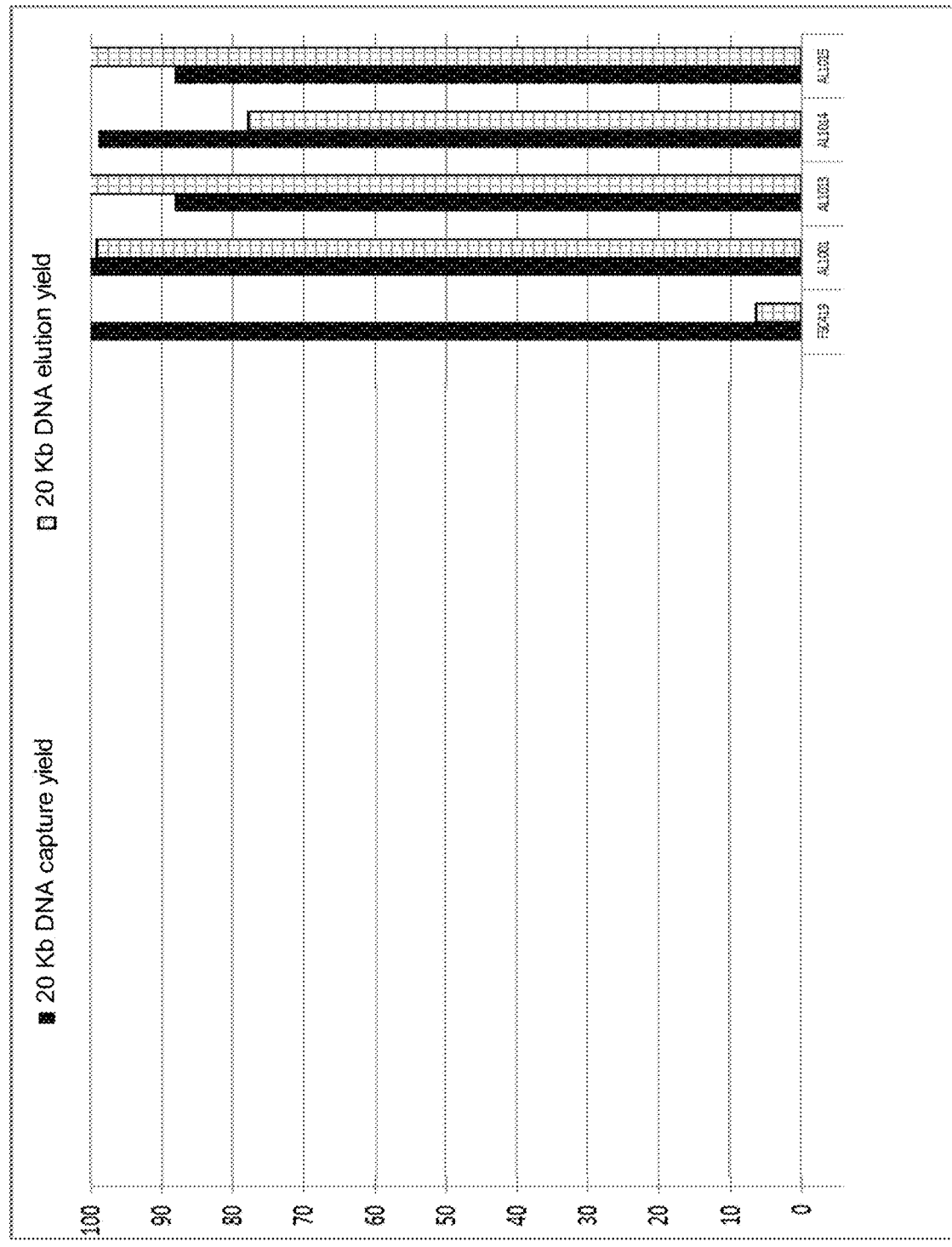

FIG. 9 represents the DNA capture yield (black) and elution yield (squared) for magnetite particles covered with inorganic silicate compounds and with compounds having an affinity for said at least one magnetic compound and/or for said at least one inorganic silicate compound:

FSC 419 corresponds to the results obtained with 100 nm magnetite particles;

AL1001 corresponds to the results obtained with 100 nm magnetite particles covered with Ludox® 6% (weight/weight) at pH 3.5;

AL1013 corresponds to the results obtained with 100 nm magnetite particles covered with Ludox® 6% (weight/weight) and with pyrophosphate ions at 6.8 mol %;

AL 1014 corresponds to the results obtained with magnetite particles covered with bentonite 30% (weight/weight) at pH 3.5;

AL1015 corresponds to the results obtained with 100 nm magnetite particles covered with bentonite 30% (weight/weight) and with pyrophosphate ions at 6.8 mol %.

Figure 10:
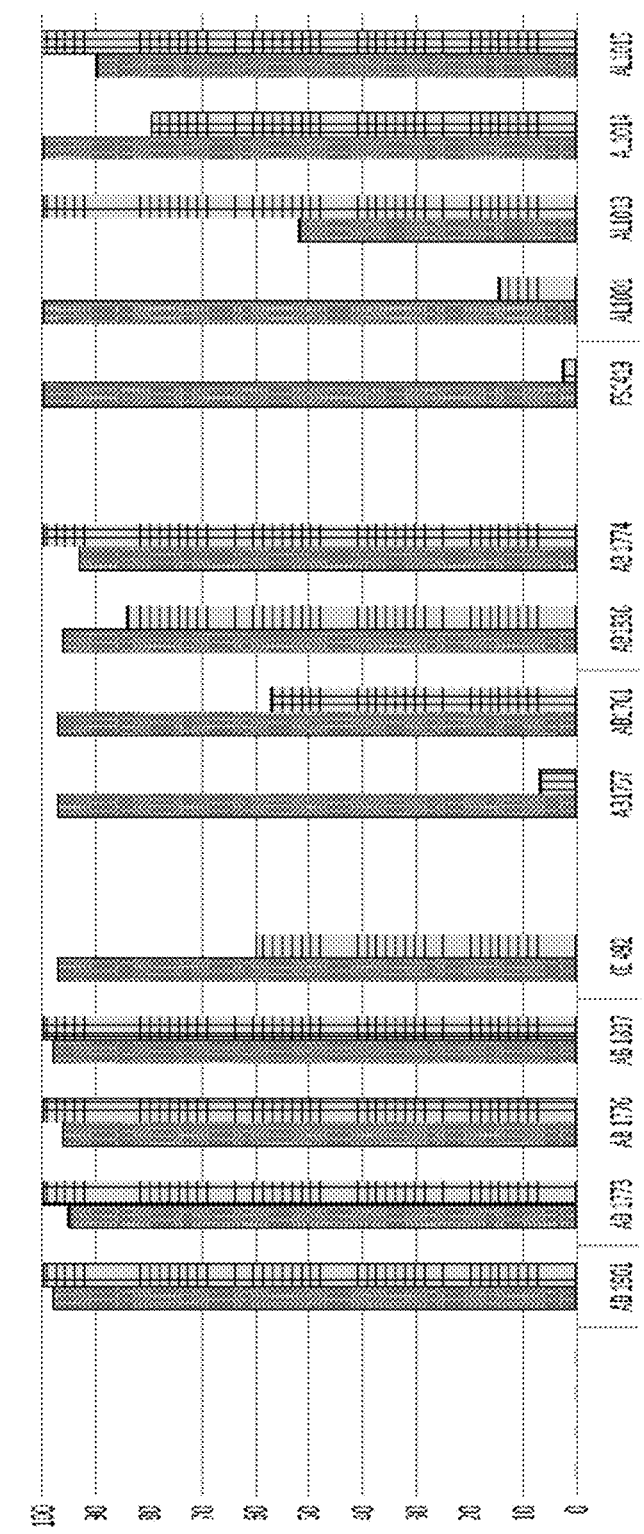

FIG. 10 represents the RNA capture yield (gray) and elution yield (squared) for magnetite particles covered with inorganic silicate compounds and with compounds having an affinity for said at least one magnetic compound and/or for said at least one inorganic silicate compound (in comparison with the references). Some particles of FIG. 9 were tested with respect to RNA and the results appear in FIG. 10. The other particles tested are listed in table 3 of example 3 below.

Figure 11:
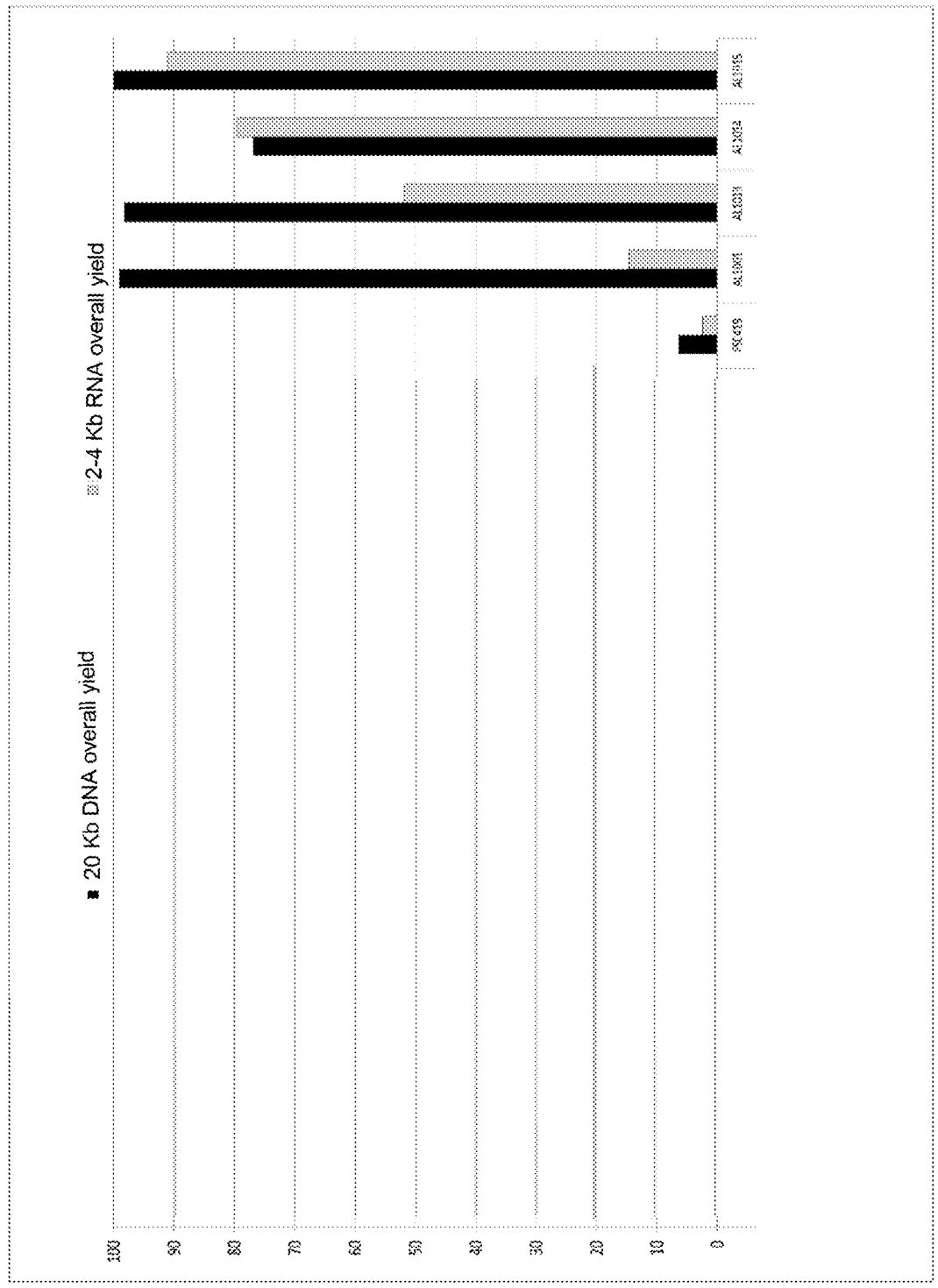

FIG. 11 represents the overall DNA extraction (black) and RNA extraction (gray) yield for magnetite particles covered with inorganic silicate compounds and with compounds having an affinity for said at least one magnetic compound and/or for said at least one inorganic silicate compound (in comparison with the references) of FIGS. 9 and 10.

Figure 12:
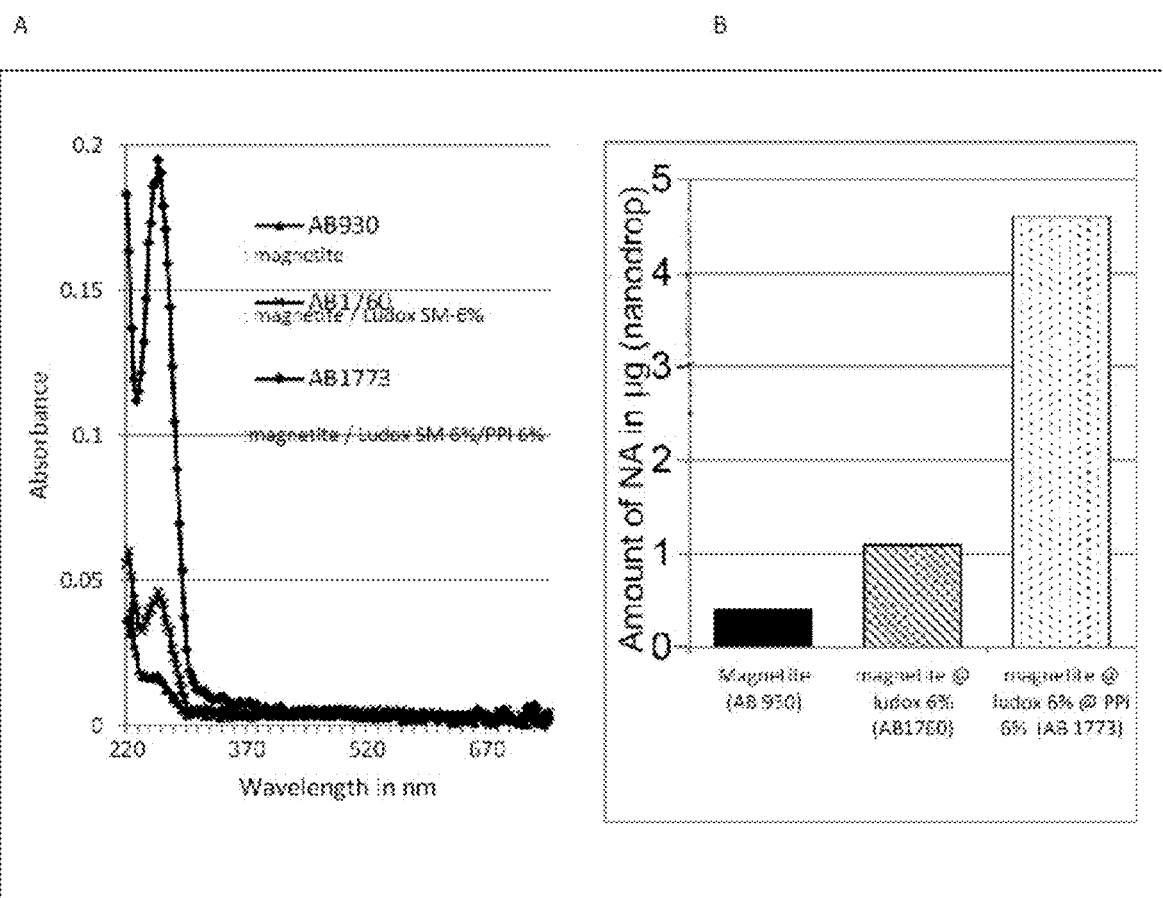

FIG. 12 represents the efficiency of extraction of nucleic acids from the blood with three-layer complexes according to the invention comprising a type of magnetite (AB 930 of 100 nm) as described in the invention (Nanodrop UV assay (ThermoScientific, Waltham, USA))

FIG. 12A represents the absorbance of three types of particles as a function of wavelength AB930: pure magnetite—curve with triangles AB1760: magnetite covered with Ludox® SM 6% weight/weight—curve with crosses, and AB1773: magnetite covered with Ludox® SM 6% then with pyrophosphate ions at 6.8 mol %—curve with diamonds.

FIG. 12B represents the amount of nucleic acids captured in the blood as a function of three different types of particles; the same as those of FIG. 12A.

Figure 13:
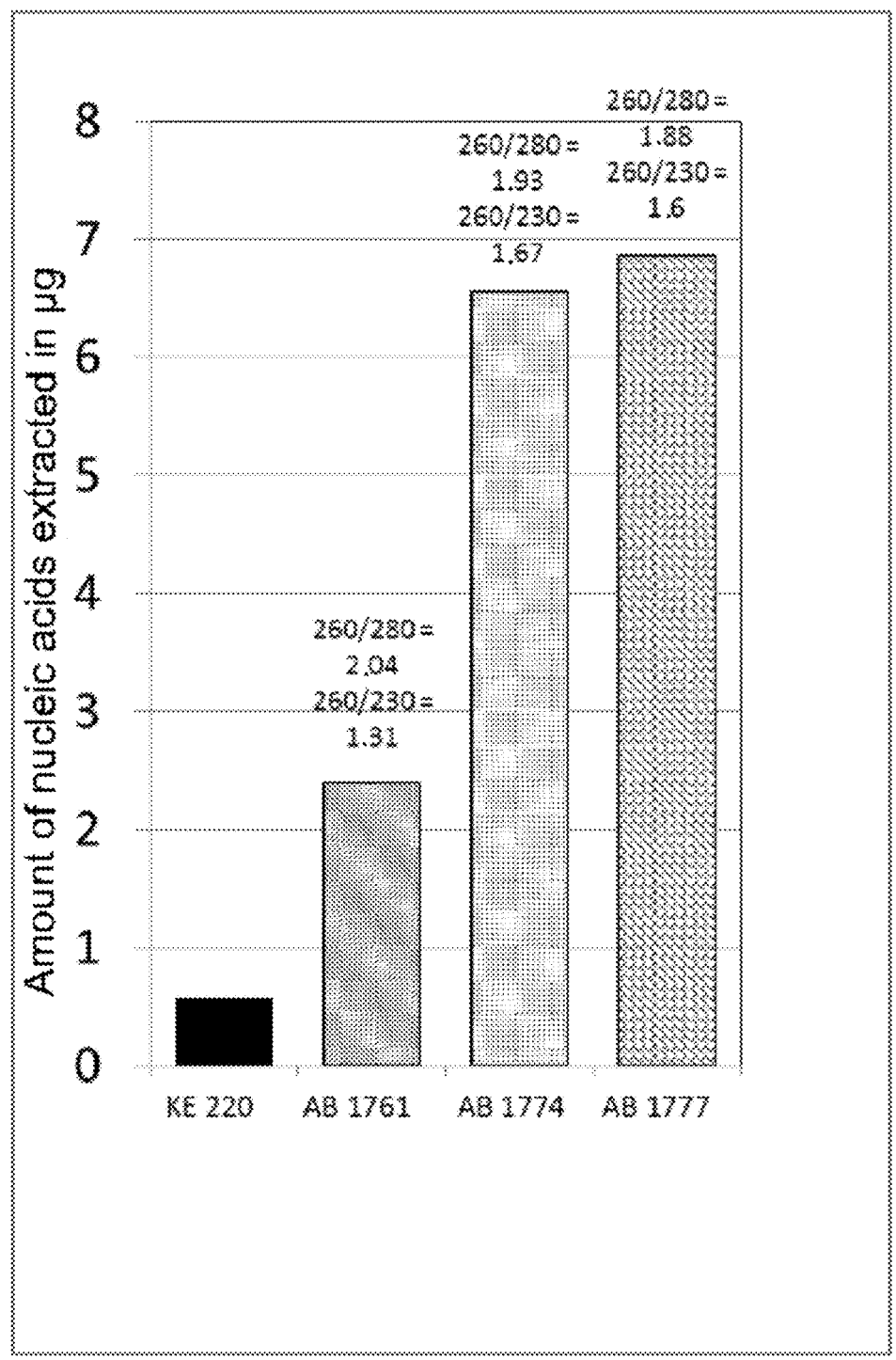

FIG. 13 illustrates the efficiency of nucleic acid extraction in the blood with three-layer complexes according to the invention comprising another type of magnetite AB 1757 50 nm as described in the invention (Nanodrop UV assay (ThermoScientific, Waltham, USA)). The four types of particles tested are the following:

KE220: magnetite coated with pyrophosphate ions at 6.8 mol %;
AB1761: magnetite coated with 6% weight/weight of Ludox®;
AB 1774: magnetite coated with Ludox 6% weight/weight and with pyrophosphate ions at 6.8 mol %, and
AB1777: magnetite coated with Ludox® at 6% weight/weight and with triphosphate ions at 6.8 mol %.

Figure 14:
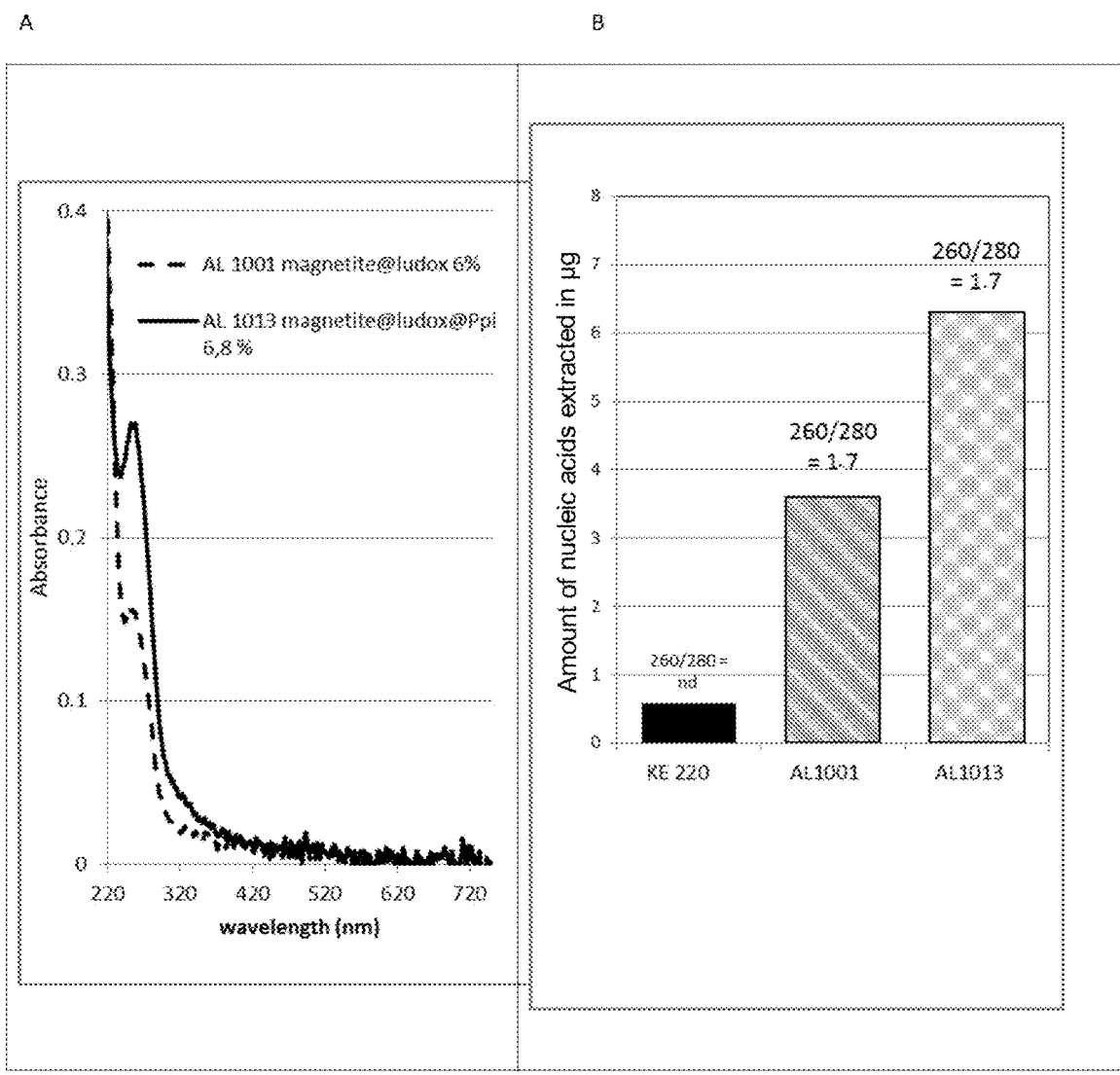

FIG. 14 illustrates the efficiency of nucleic acid extraction in the blood with three-layer complexes according to the invention comprising another type of magnetite FSC 419 100 nm as described in the invention (Nanodrop UV assay (ThermoScientific, Waltham, USA)).

FIG. 14A represents the absorbance of two types of particles as a function of the wavelength:

AL1001: magnetite covered with Ludox® 6% weight/weight—dashed line, and
AL1013: magnetite covered with Ludox® 6% then with pyrophosphate ions at 6.8 mol %—solid curve.

FIG. 14B represents the amount of nucleic acids captured in the blood as a function of three different types of particles: KE220: magnetite coated with pyrophosphate ions at 6.8 mol %; the same two types of particles as those of FIG. 14A.

Figure 15:
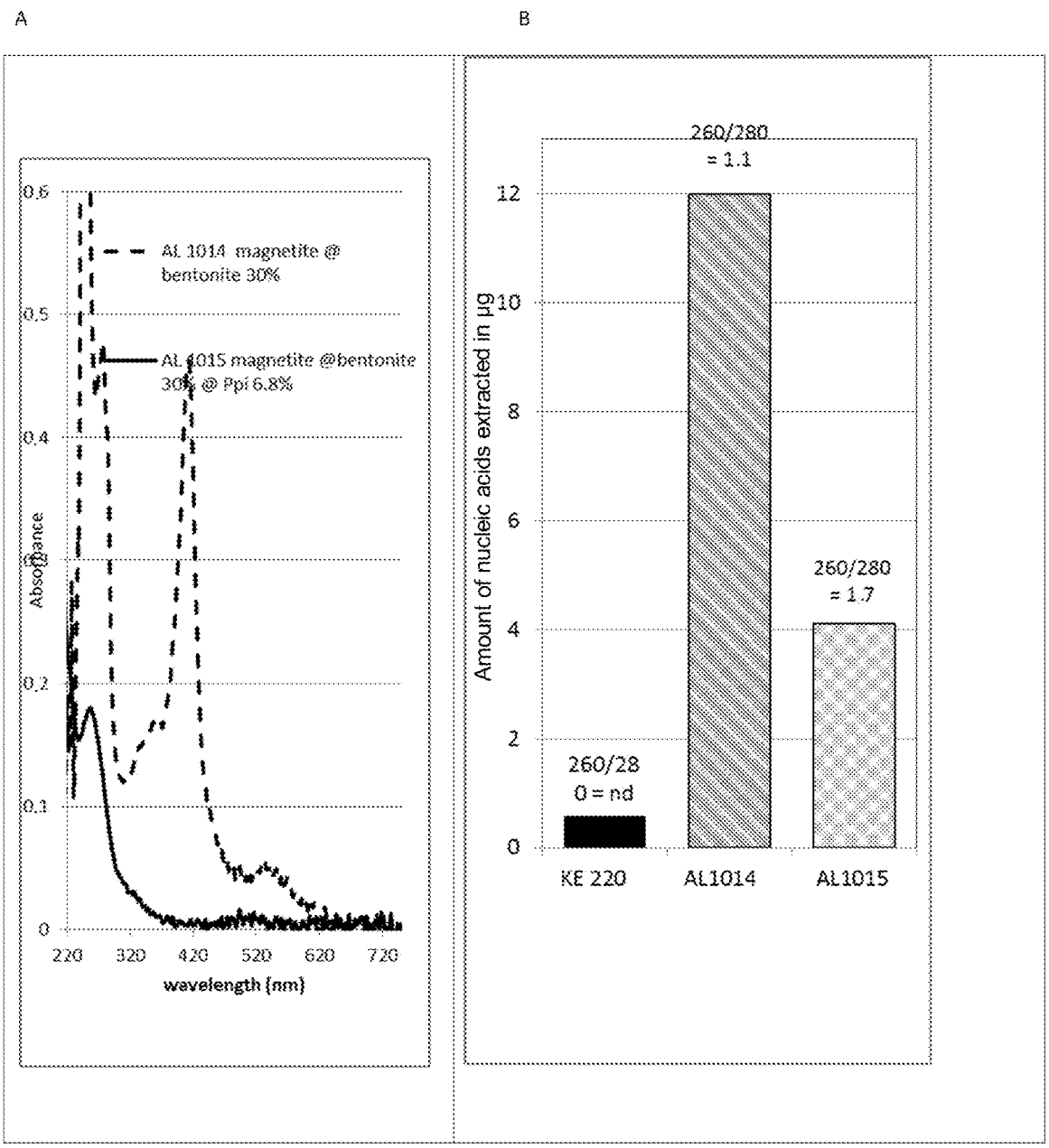

FIG. 15 illustrates the efficiency of nucleic acid extraction in the blood with three-layer complexes according to the invention comprising another type of inorganic silicate compound: bentonite as described in the invention (Nanodrop UV assay (ThermoScientific, Waltham, USA)).

FIG. 15A represents the absorbance of two types of particles as a function of the wavelength:

AL1014: magnetite covered with bentonite 30% weight/weight—dashed line,
AL1015: magnetite covered with bentonite 30% then with pyrophosphate ions at 6.8 mol %—solid curve.

FIG. 15B represents the amount of nucleic acids captured in the blood as a function of three different types of particles: KE220: magnetite coated with pyrophosphate ions at 6.8 mol %; the same two types of particles as those of FIG. 15A.

Figure 16:
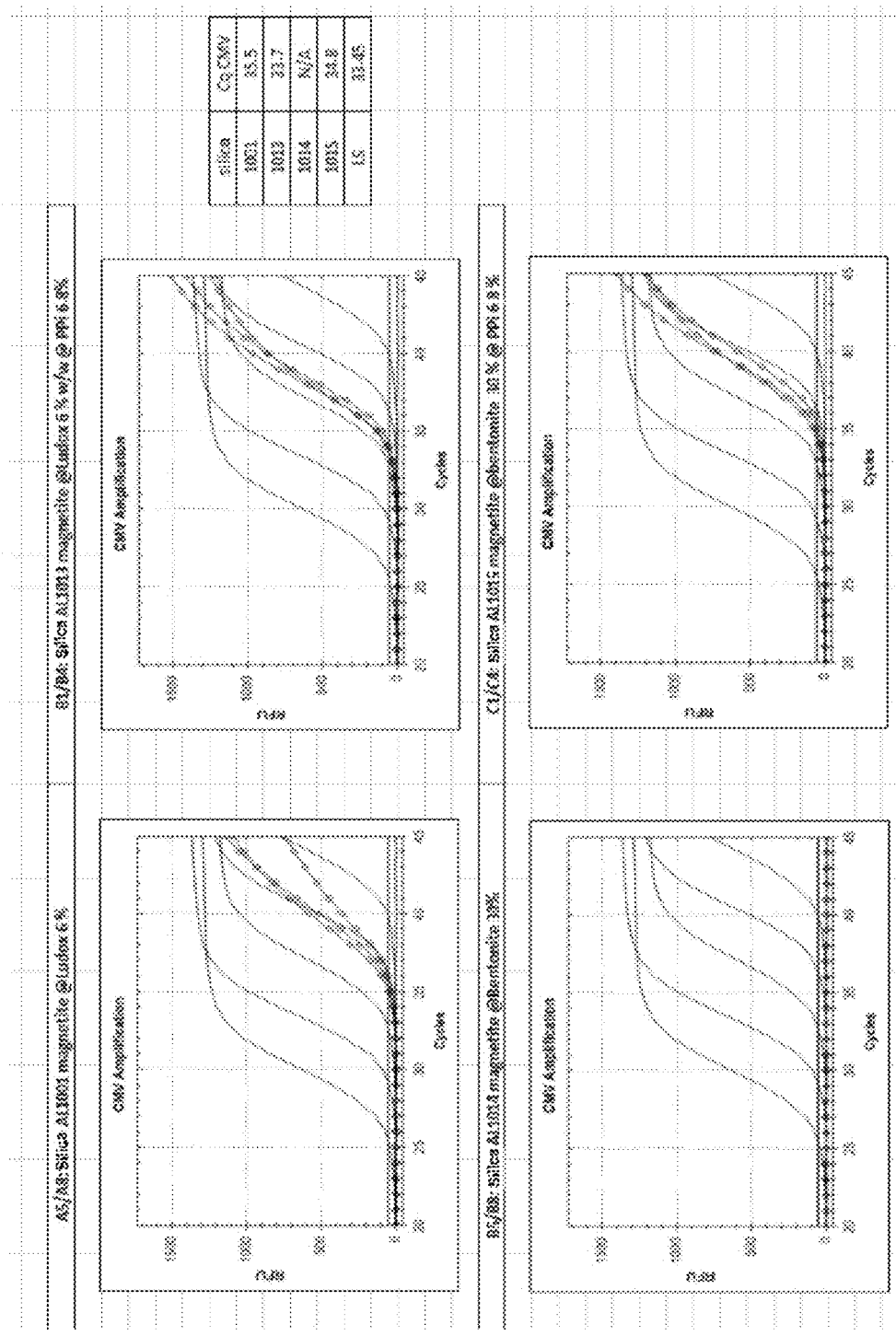

FIG. 16 illustrates the results of a PCR amplification of CMV virus DNA extracted by various different types of magnetic particles which have been singly coated (two-layer complexes) or doubly coated (three-layer complex according to the invention).

AL1001: magnetite coated with Ludox 6%;
AL1013: magnetite coated with Ludox 6% weight/weight and with pyrophosphate ions at 6.8 mol %;
AL1014: magnetite coated with bentonite at a 30% weight/weight ratio;
AL1015: magnetite coated with bentonite at a 30% weight/weight ratio and then with pyrophosphate ions at 6.8 mol %.

EXAMPLES

Example 1: Coating of Magnetite Particles with Inorganic Silicate Compounds (Magnetite/Inorganic Silicate Compounds)

Magnetite particles of approximately 100 nm were coated with commercial inorganic silicate compounds using various magnetite/silica ratios. In the examples below, Ludox SM® of 7 nm, bentonite, magnesium or sodium silicate, "fumed" silica or silicon dioxide were used.

The coating is promoted by opposite electrostatic interactions. Thus, the latter must be carried out in a pH range where the inorganic silicate particles and the magnetite have opposite surface charges.

The isoelectric point of the magnetite is at 6.8 and that of the silica is around 2. The coating must be carried out at a pH of between 2 and 6.8, that is to say at a selected pH of 3.5 as described below.

A—Magnetite Coating Protocol:

1—From 1 to 400 mg of magnetite (11-814 µl at 92.1 mg/ml) are washed and taken up in the same volume with a solution of HCl at 1 mM, pH 3, in order to adjust the pH of the suspension. The volume of the washing solution depends on the amount of magnetite (between 2 ml (1-75 mg of magnetite) and 10 ml (400 mg of magnetite)).

2—The solutions of inorganic silicate compounds indicated above are prepared in water and their pH is adjusted to approximately 3 by adding a few drops of 1M HCl before adjusting their concentrations to between 30 and 300 mg/ml.

3—The suspensions of magnetite and of inorganic silicate compounds are mixed in the ratios indicated in table 1 below and mixing is performed by vortexing immediately before adjusting the volume, with a solution of HCl at 1 mM, pH 3, between 2 ml and 10 ml according to the amount of magnetite used. Table 1 gives a few examples of coating of the magnetite with inorganic silicate nanoparticles carried out with magnetite/silica (weight/weight) ratios of between 1% and 50% in order to obtain nanocomposites having different degrees of coverage.

4—The pH of the final suspension is verified and must be around 3-3.5 and, depending on the type of inorganic silicate compound, it may be necessary to adjust the pH with a few µl of NaOH or of HCl at 1M.

5—The suspension is stirred on a roll mixer for one to two hours at ambient temperature.

6—A negative control can be carried out in the same way, but with a solution of sodium hydroxide at pH=9-11 (100 µM-1.5 mM of NaOH) and without adjusting the pH of the inorganic silicate compounds. At this pH, the nanoparticles of silica and of magnetite are both negatively charged and the silica does not coat the magnetite.

B—Protocol for Washing the Suspension of Magnetite/Inorganic Silicate Compound Particles 1. The supernatant is removed by magnetization of the newly formed magnetite/silicate nanoparticle composite particles. The suspension is washed first with water by magnetization and then using a sodium hydroxide solution at 100 µM, pH 9 and then taken up in the same solution and is optionally subjected to ultrasound for 10 min at 100% power (Vibra-cell 75042, Bioblock Scientific, Illkirch, France). The sodium hydroxide solution is removed from the solution by magnetization. These steps are carried out three times or even more until a pH of 9 is reached.

2. The solution of particles is washed with water by successive magnetization three times until a pH of 7 is reached, and then concentrated to 50 mg/ml. The solids content is measured in order to verify this concentration.

TABLE 1

Experimental details of the simple coating of the magnetite with silicates

| | Carrier magnetite particle | | Inorganic silicate compounds | | Silica/magnetite ratio | | IEP |
|---|---|---|---|---|---|---|---|
| | Type of magnetite | Weight used | Type of nanoparticles | Weight used | (weight/weight) | Grafting pH | (Isoelectric point) |
| AL 1001-CTRLE) | Magnetite FSC 419 100 nm 92.1 mg/ml. 814 μl | 75 mg | ludox SM 7 nm (Sigma Aldrich, ref. 420794) in solution in water at 30% at pH 9.5 | 15 μl (4.5 mg) | 6% | 11 | 7.5 |
| KE 59 | Magnetite AB 930/100 nm | 75 mg | ludox SM 7 nm (Sigma Aldrich, reference 420794) in solution in water at 30% at pH 9.5 | 0.75 mg | 1% | 3-4 | 5.2 |
| KE 58 | Magnetite AB 930 100 nm | 75 mg | idem | 2.25 mg | 3% | 3-4 | 3.8 |
| AB 1760 | Magnetite AB 930 100 nm | 400 mg | idem | 29 mg | 6% | 3-4 | 2 |
| AL 1001 | Magnetite FSC 419 100 nm | 75 mg | idem | 15 μl (4.5 mg) | 6% | 3-4 | 4 |
| AB 1761 | Magnetite AB 1757 50 nm | 400 mg | idem | 29 mg | 6% | 3-4 | nd |
| AL 1009 | Magnetite FSC 419 100 nm | 5 mg | bentonite (Aldrich 285234) 50 mg/ml in water at pH 10.4 | 6 μl (0.3 mg) | 6% | 3-4 | <1 |
| AL. 1014 | Magnetite FSC 419 100 nm | 75 mg | bentonite (Aldrich 285234) 100 mg/ml in water adjusted to pH 7 with 1M HCl | 318 μl (32 mg) | 30% | 3 | <1 |
| AL. 1018 | Magnetite FSC 419 100 nm | 75 mg | Magnesium trisilicate (Aldrich 63148) 150 mg/ml in water adjusted to pH 7 with 1M HCl | 500 μl (75 mg) | 50% | 3 | 5.5 |
| AB 1992 | Magnetite AB 930 100 nm | 150 mg | Magnesium trisilicate (Aldrich 63148) | 72 mg | 50% | 3-4 | nd |
| AB 1024 | Magnetite AB 930 100 nm | 75 mg | Sodium trisilicate (Aldrich 63148) | 500 μl (75 mg) | 50% | 3 | 5.1 |
| AB 1959 | Magnetite AB 930 100 nm | 150 mg | Fumed silica (Aldrich S5130) | 18 mg | 10% | 3-4 | nd |
| AB 1960 | Magnetite AB 930 100 nm | 150 mg | Silicon dioxide (Aldrich 637238) | 18 mg | 10% | 3-4 | nd |

C—Physicochemical Characterization by Zetametry

The nanoparticles synthesized are analyzed by zetametry on the Zetasizer Nano ZS apparatus from Malvern Instruments (Malvern, United Kingdom) in order to measure their isoelectric point. The measurements are carried out at 0.3 mg/ml in three different solutions, respectively:

5 mM HCl, 10 mM NaCl, pH 2.5;
Tris, 5 mM HCl, 10 mM NaCl, pH 7;
and 5 mM NaOH, 10 mM NaCl, pH 11.5.

For this, 6 μl of the suspension of particles at 50 mg/ml (0.3 mg) in water are taken and added to 2 ml of one of the above solutions contained in a polypropylene bottle in order to obtain a suspension at 0.15 mg/ml. The pH is measured so as to be sure that the pH of the solution has not been modified by the addition of the particles. The suspension of particles is then introduced into the measurement cuvette (Folded capillary cells, DTS 1061) using a 2 ml syringe. The measuring program chosen for all of the Zeta potential measurements is the "BMX Zeta" program (the measurements are carried out at 21° C.).

The measurement of the zeta potential of these particles as a function of the pH makes it possible to deduce therefrom the isoelectric point when the zeta potential becomes zero. It is an indication of the state of surface functionalization of the magnetite.

Conclusion:

In general (cf. table 1), a clear shift in the isoelectric point of the magnetite toward lower values is demonstrated, clearly corresponding to a coating with inorganic silicate compounds, the coating level of which can be adjusted by the concentration of inorganic silicate compound (see for this experiments KE 59, KE 58 or AB 1760 wherein the isoelectric point evolves as a function of the concentration of Ludox® inorganic silicate compound particles) or AL 1018 and AL 1024 as a function of the magnesium trisilicate or sodium trisilicate concentration.

Example 2: Coating of Magnetite Particles with Compounds Having an Affinity for the at Least One Magnetic Compound and/or for the at Least One Inorganic Silicate Compound. For Greater Simplicity, the Latter Compounds are Also Called Ligands (Magnetite/Ligand)

Magnetite particles were coated with ligands as described hereinafter according to two protocols as a function of the pKa values of the compounds having an affinity for the at least one magnetic compound and/or for the at least one inorganic silicate compound (ligands) chosen.

As for the adsorption of the inorganic silicate nanoparticles, an iron ligand will adsorb efficiently onto the magnetite in a pH range wherein the ligand is negatively charged and wherein the magnetite is positively charged, that is to say at a pH between the first pKa of the ligand and the isoelectric point of the magnetite (6.8).

According to this principle, the coatings of compounds having an affinity for said at least one magnetic compound and/or for said at least one inorganic silicate compound of phosphate type (pKa between 1 and 12) and phosphonate type (pKa between 3 and 6) were carried out respectively with a pH of the solution equal to pH 3 or pH 5. It should be noted that any other compound having an affinity for said at least one magnetic compound and/or for said at least one inorganic silicate compound can be adsorbed (carboxylic acids, etc.) according to this principle.

The two protocols are described below.

Protocol for Coating Magnetite at pH=3 with Compounds Having an Affinity for the at Least One Magnetic Compound and/or for the at Least One Inorganic Silicate Compound of Phosphate Type 1—A minimal volume of magnetite of about 550 μl, corresponding to a weight of about 1 to 80 mg, is washed with a solution of HCl at 1 mM, pH 3, and then taken up in the same solution before being introduced into a 1.5 ml polypropylene microtube.

2—The ligand of phosphate type in solution in water at 40 mM, the pH of which has been adjusted to pH 3, is added with vortexing so as to correspond to a molar fraction of between 0.1 mol % and 10 mol % relative to the iron.

Example

Molar fraction of ligand relative to iron =

$$\frac{\text{number of moles of ligand}}{(\text{number of moles of ligand}) + (\text{number of moles of Fe3O4} \times 3)} =$$

$$\frac{V_{ligand} \times [\text{ligand}]}{(V_{ligand} \times [\text{ligand}]) + \left(\frac{\text{weight Fe3O4}}{M(\text{Fe3O4})} \times 3\right)}$$

3—The pH is controlled using a pH-meter; it must be about 3. It is not generally necessary to readjust the pH, but this can be done, if required, with a few μl of NaOH or HCl at 0.1 M.

4—The volume is made up to 1.5 ml with a solution of HCl at 1 mM, pH 3.

5—The Eppendorf tube is stirred on a roll for two hours at ambient temperature.

6—The reaction medium is then washed with water by magnetization until a pH of 7 is obtained.

7—The particles are taken up in the appropriate amount of water in order to obtain a concentration of 50 mg/ml (verified by measuring the solids content).

Protocol for Coating the Magnetite at pH=5 with Compounds Having an Affinity for Said at Least One Magnetic Compound and/or for Said at Least One Inorganic Silicate Compound of Phosphonate Type 1—A minimal volume of magnetite of about 550 μl, corresponding to a weight of about 30-80 mg, is washed with a solution of HCl at 10 μM, pH 5, and then taken up in the same solution before being introduced into a 1.5 ml Eppendorf tube.

2—The ligand in solution in water at 40 mM, the pH of which has been adjusted to pH 5, is added with vortexing so as to correspond to a molar fraction of between 0.1 mol % and 10 mol % relative to the iron.

3—The pH is controlled using a pH-meter and then adjusted to around 5, if required, with a solution of sodium hydroxide or of HCl at 0.1 M.

4—The volume is made up to 1.5 ml with a solution of HCl at 10 μM, pH 5.

5—The reaction mixture is stirred with a thermomixer for 12 hours at 60° C.

6—The particles are then washed with water by magnetization until a pH of 7 is obtained.

7—The nanoparticles are taken up in the appropriate amount of water in order to obtain a concentration of 50 mg/ml (verified by measuring the solids content).

The table below gives a summary of a few examples of coating of the magnetite with compounds having an affinity for said at least one magnetic compound and/or for said at least one inorganic silicate compound (at optimal concentration with respect to the ligand compound so as to comply with the best conditions for extraction of the nucleic acids).

TABLE 2

Experimental detail of the simple coating of the magnetite with compounds having an affinity for the at least one magnetic compound and/or for the at least one inorganic silicate compound

| | Carrier magnetite particle | | Compounds having an affinity for said at least one magnetic compound and/or for said at least one inorganic silicate compound (ligand) | | | | |
|---|---|---|---|---|---|---|---|
| | Type of magnetite | Weight used | Type of ligand | Volume used at 40 mM | Fe/ligand molar ratio | Grafting pH | IEP |
| KE 54a | Magnetite AB 930 100 nm | 80 mg | Orthophosphoric acid (Aldrich ref.: 345245) | 1900 µl | 6.8% | 3.5 | 5.2 |
| KE 220 | idem | 80 mg | Sodium pyrophosphate (Aldrich ref.: 221368) | 1900 µl | 6.8% | 3.5 | <2 |
| KE 351 | idem | 80 mg | Sodium triphosphate (Aldrich ref.: 72061) | 1900 µl | 6.8% | 3.5 | 3.2 |
| KE 225 | Idem | 80 mg | HEEEPA = (2-(2-(2-Hydroxyethoxy)ethoxy)ethyl)phosphonic acid (Sikemia, Montpellier, France) | 1900 µl | 10% | 5 | 4.3 |
| KE 231 | Idem | 80 mg | NTPA Nitrilotris(methylene) triphosphonic acid (Acros, Geel, Belgium) | 1900 µl | 0.1% | 5 | nd |

Conclusion:

A clear shift in the value of the isoelectric point toward lower values than that of the magnetite (isoelectric point IEP: 6-7) is observed, thereby demonstrating the coating of the magnetite and the modification of its surface charge and thus of its surface properties.

Example 3: Coating with Compounds Having an Affinity for the at Least One Magnetic Compound and/or for the at Least One Inorganic Silicate Compound of Magnetite Particles Precoated with Inorganic Silicate Compounds (Magnetite/Inorganic Silicate Compounds/Ligands)

The magnetite/inorganic silicate compound composite particles obtained in example 1 are in turn coated with compounds having an affinity for the at least one magnetic compound and/or for the at least one inorganic silicate compound exactly as described in example 2, except that it is magnetite/inorganic silicate compound particles which are used instead of the magnetite alone (cf. table 3). As in example 2, two coating protocols are used according to the pKa of the compound having an affinity for the at least one magnetic compound and/or for the at least one inorganic silicate compound (ligand). Isoelectric point measurements are carried out on these particles.

TABLE 3

Experimental detail of the coating of the magnetite/inorganic silicate compounds with compounds having an affinity for the at least one magnetic compound and/or for the at least one inorganic silicate compound

| | Carrier magnetite particle | | Compounds having an affinity for said at least one magnetic compound and/or for said at least one inorganic silicate compound (ligand) | | | | |
|---|---|---|---|---|---|---|---|
| | Type of magnetite | Weight used | Type of ligand | Volume used at 40 mM | Fe/ligand molar ratio | Grafting pH | Zeta potential at pH 7 |
| AB1961 | Magnetite 100 nm/Ludox ® 6% (AB 1760) | 30 mg | Pi = phosphate ion | 710 µl | 6.8% | 3.5 | nd |
| AB 1773 | idem | 30 mg | PPi = pyrophosphate ion | 710 µl | 6.8% | 3.5 | nd |
| AB 1776 | idem | 30 mg | PPPi = triphosphate ion | 710 µl | 6.8% | 3.5 | nd |
| KE 492 | idem | 30 mg | HEEEPA = (2-(2-(2-Hydroxyethoxy)ethoxy)ethyl)phosphonic acid (Sikemia, Montpellier, France) | 1420 µl | 10% | 5.6 | nd |
| AB1837 | idem | 30 mg | NTPA Nitrilotris(methylene) triphosphonic acid (Acros, Geel, Belgium) | 14.2 µl | 0.1% | 5.3 | |

TABLE 3-continued

Experimental detail of the coating of the magnetite/inorganic silicate compounds with compounds having an affinity for the at least one magnetic compound and/or for the at least one inorganic silicate compound

| | Carrier magnetite particle | | Compounds having an affinity for said at least one magnetic compound and/or for said at least one inorganic silicate compound (ligand) | | | | |
|---|---|---|---|---|---|---|---|
| | Type of magnetite | Weight used | Type of ligand | Volume used at 40 mM | Fe/ligand molar ratio | Grafting pH | Zeta potential at pH 7 |
| AL 1013 | Magnetite 100 nm/ Ludox ® 6% (AL 1001) | 30 mg | PPi | 875 µl | 8.3% | 3 | 1.5 |
| AB 1774 | Magnetite 50 nm/ Ludox ® 6% (AB 1761) | 30 mg | PPi | 710 µl | 6.8% | 3.6 | nd |
| AB 1836 | idem | 30 mg | HEEEPA | 1420 µl | 10% | 5.6 | nd |
| AB1777 | idem | 30 mg | PPPi | 710 µl | 6.8% | 3.2 | nd |
| AL 1015 | Magnetite 100 nm/ bentonite 30% (AL 1014) | 37 mg | PPi | 1080 µl | 8.3% | 3 | <1 |

Conclusion:

the measurement of the isoelectric point shows that the coating with said at least one compound having an affinity for said at least one magnetic compound and/or said at least one inorganic silicate compound barely modifies the surface charge of the particles. This demonstrates that the particles remain negatively charged at pH 7.

Example 4: Measurements of the DNA and RNA Extraction Yields with Magnetic Particles Coated with Inorganic Silicate Compounds Described in Example 1

In order to measure the capacities and the performance levels of the magnetic particles coated with inorganic silicate compounds, described in example 1, in terms of nucleic acid extraction, the protocol described below was used with the nucleic acids described in table 4.

TABLE 4

| Nucleic acids used in the nucleic acid extraction test | | | |
|---|---|---|---|
| Nucleic acid | Name of supplier | Reference | Mean size |
| Salmon testes DNA | Sigma, St Louis, USA | D1626-1G | 20 Kb |
| Human placenta DNA | Fluka, Buchs, Switzerland | 31167 | 20 Kb |
| Human RNA from MRC2 cells | R&D Biotech, Besançon, France | | 2-4 Kb |

Measurement of the Capture Yield

1—The following solution is prepared in a 1.5 ml polypropylene microtube:
  a—100 µl of 8M guanidinium chloride (GuHCl) buffered with Tris HCl at 50 mM, pH 7 (pH rigorously remeasured before the manipulation).
  b—30 µl of Tris HCl at 100 mM, pH 7.
  c—20 µl (20 µg) of the solution of nucleic acids at 1 mg/ml in 50 mM of Tris HCl, pH 7 (in the case of DNA) or at 1 mg/ml in water in the case of RNA.
  d—Mixing is carried out by vortexing.

2—50 µl of the particles prepared in example 1 described previously at 50 mg/ml in water (2.5 mg) are added extemporaneously. The final conditions are: 100 µg/ml of nucleic acids per 2.5 mg of particles in 200 µl of 4M GuHCl, 45 mM Tris HCl, pH 7).

3—The mixture is left to stir on a stirrer (Thermomixer, Eppendorf, Le Pecq, France) at 1000 rpm at 25° C. for 15 min.

4—An optical density OD measurement is carried out at 260 nm.

5—After magnetization, 1.7 µl of the supernatant of the suspension are removed and are assayed by UV spectrophotometry at 260 nm using a Nanodrop (ThermoScientific, Waltham, USA) in order to determine the nucleic acid concentration thereof.

6—The nucleic acid concentration of the solution is compared with that of a reference solution, starting solution, prepared without particles, in order to measure the capture yield:

Capture yield at 15 min =

$$\frac{\text{Initial } OD\ 260\ \text{nm} - \text{Residiual } OD\ O260\ \text{nm (15 min)}}{\text{Initial } OD\ 260\ \text{nm}}$$

Elution Yield Measurement

The particles on which the nucleic acids are immobilized are then washed by magnetization.

1—The suspension previously prepared is magnetized and the supernatant is discarded.

2—185 µl of a solution of 4M GuHCl, 50 mM Tris HCl, pH 7 are added. Mixing is carried out by vortexing, the mixture is magnetized and the supernatant is removed while verifying by Nanodrop UV assay (ThermoScientific, Waltham, USA) that it does not contain nucleic acids.

3—185 µl of the NucliSENS easyMAG Extraction Buffer 2 (Ref BMX 280131, bioMérieux, Marcy l'Etoile, France) are added. Mixing is carried out by vortexing, the mixture is magnetized and the supernatant is removed while verifying by Nanodrop UV assay (ThermoScientific, Waltham, USA) that it does not contain nucleic acids.

4—185 µl of the NucliSENS easyMAG Extraction Buffer 3 (ref BMX 280132, bioMérieux, Marcy l'Etoile, France) are added, mixing is carried out by vortexing, the mixture is magnetized and the supernatant is removed while verifying by Nanodrop UV assay (ThermoScientific, Waltham, USA) that it does not contain nucleic acids.

5—185 µl of the NucliSENS easyMAG Extraction Buffer 3 (ref BMX 280132, bioMérieux, Marcy l'Etoile, France) are added, mixing is carried out by vortexing and the mixture is incubated at 70° C. at 1000 rpm for 10 min.

6—The mixture is magnetized and the nucleic acid concentration is measured using the Nanodrop (ThermoScientific, Waltham, USA) at 260 nm in order to calculate the elution yield.

Elutian yield at 15 min =

$$\frac{OD\ 260\ nm\ \text{after 15 min of elution}}{\text{Initial }OD\ 260\ nm - \text{Residual }OD\ 260\ nm\ (15\ \text{min})}$$

Figure 1:
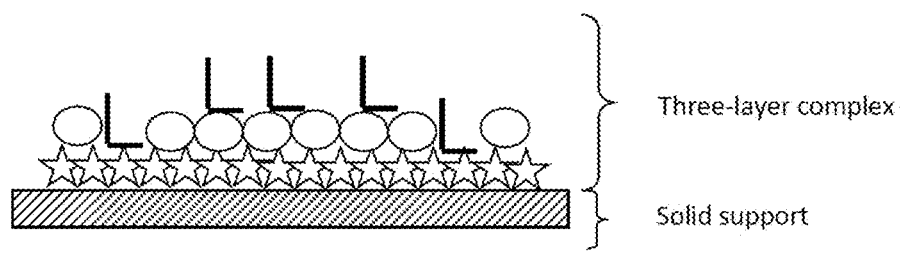
Figure 2:
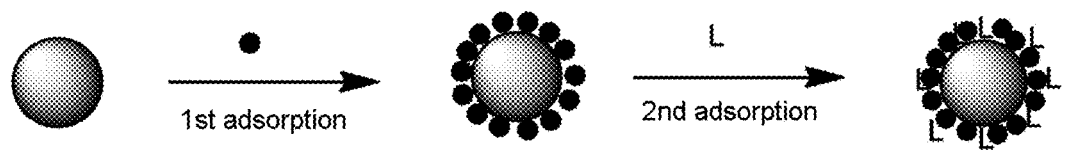
Figure 3:
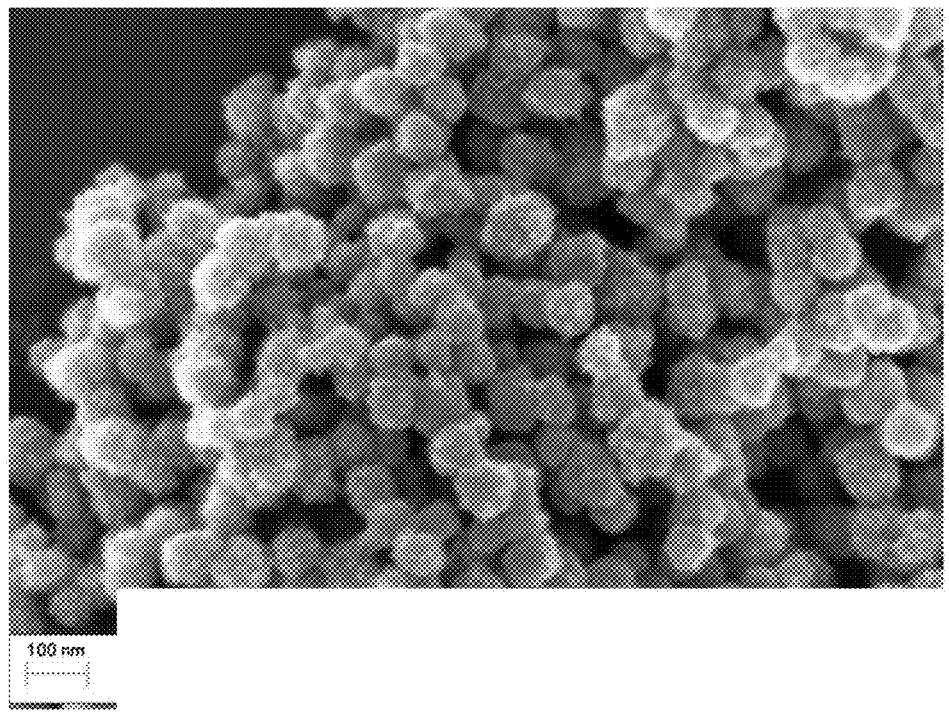
Figure 4:
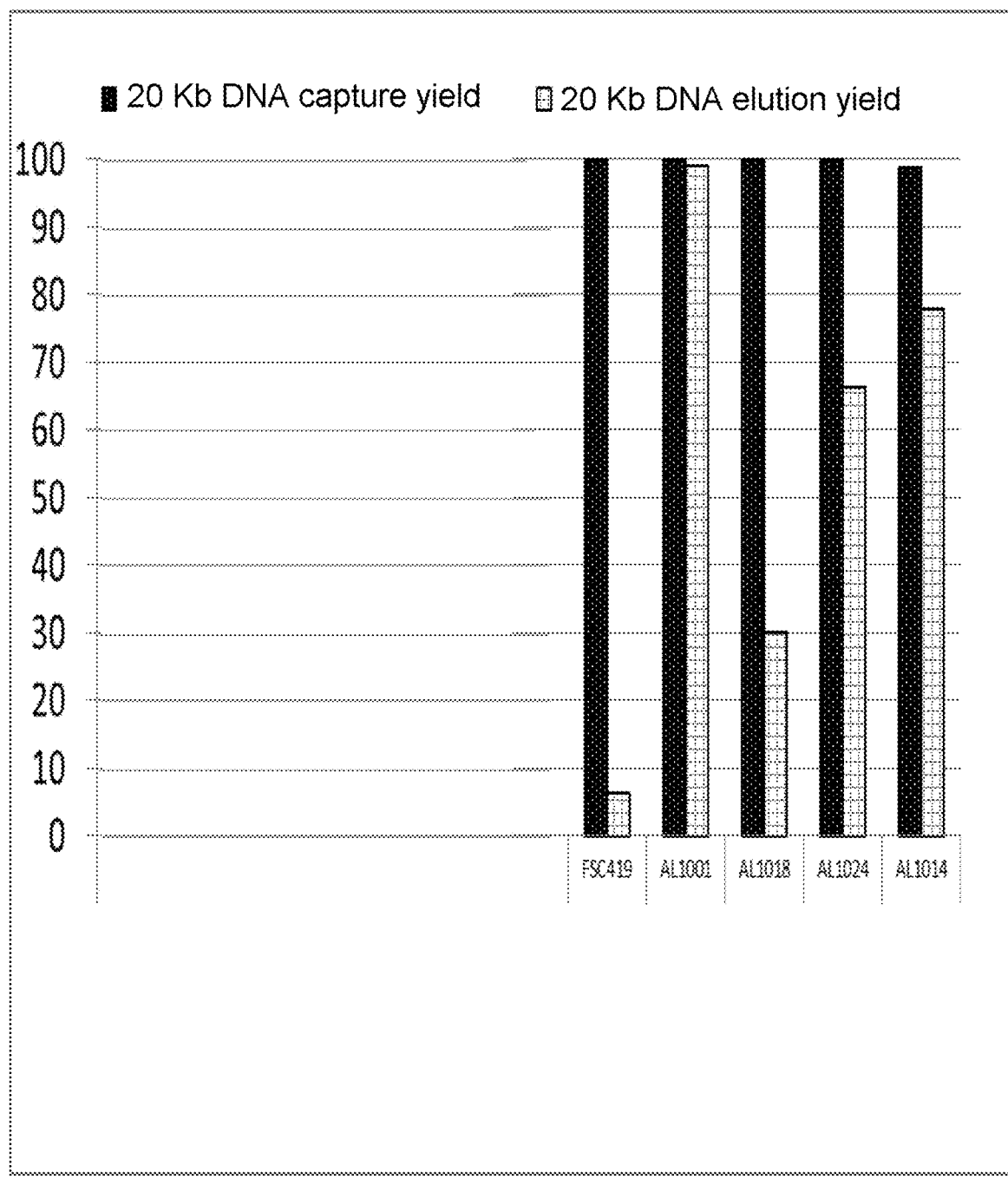
Figure 5:
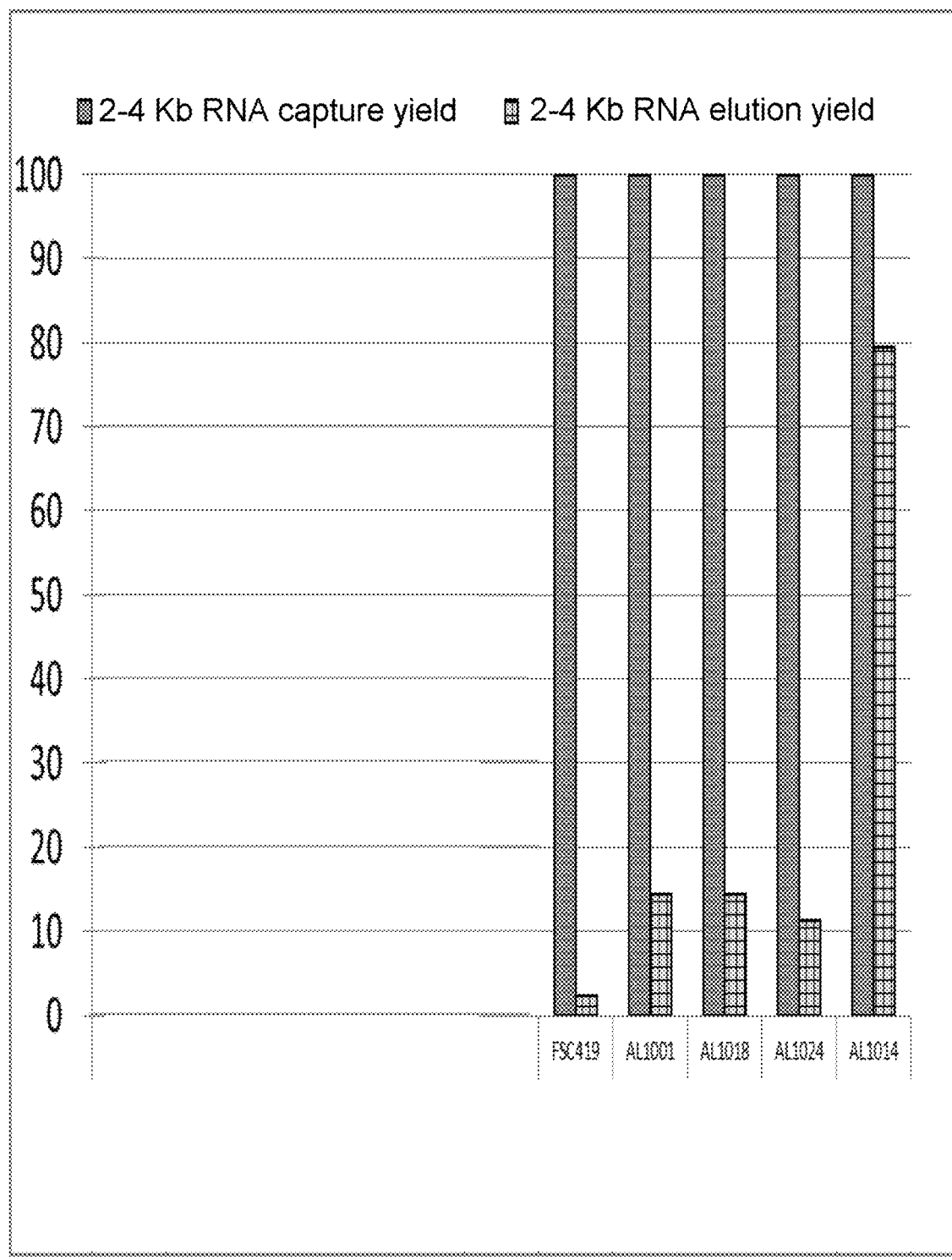
FIG. 5 represents the RNA capture yield (gray) and elution yield (squared) for magnetite particles covered with inorganic silicate compounds. The same particles as those of FIG. 4 were tested.

The protocol described above makes it possible to measure a capture yield and an elution yield, based on what has been captured, as represented in FIGS. 4 and 5. It is thus demonstrated that, with respect to magnetite, the DNA capture is only slightly modified by the coating of inorganic silicate compounds, but that its elution is notably improved. On the other hand, there is no modification of the RNA capture and the coating of inorganic silicate compound also assists in its elution (to a lesser degree). This phenomenon can be generalized to various types of inorganic silicate compounds as represented in the figures.

Figure 6:
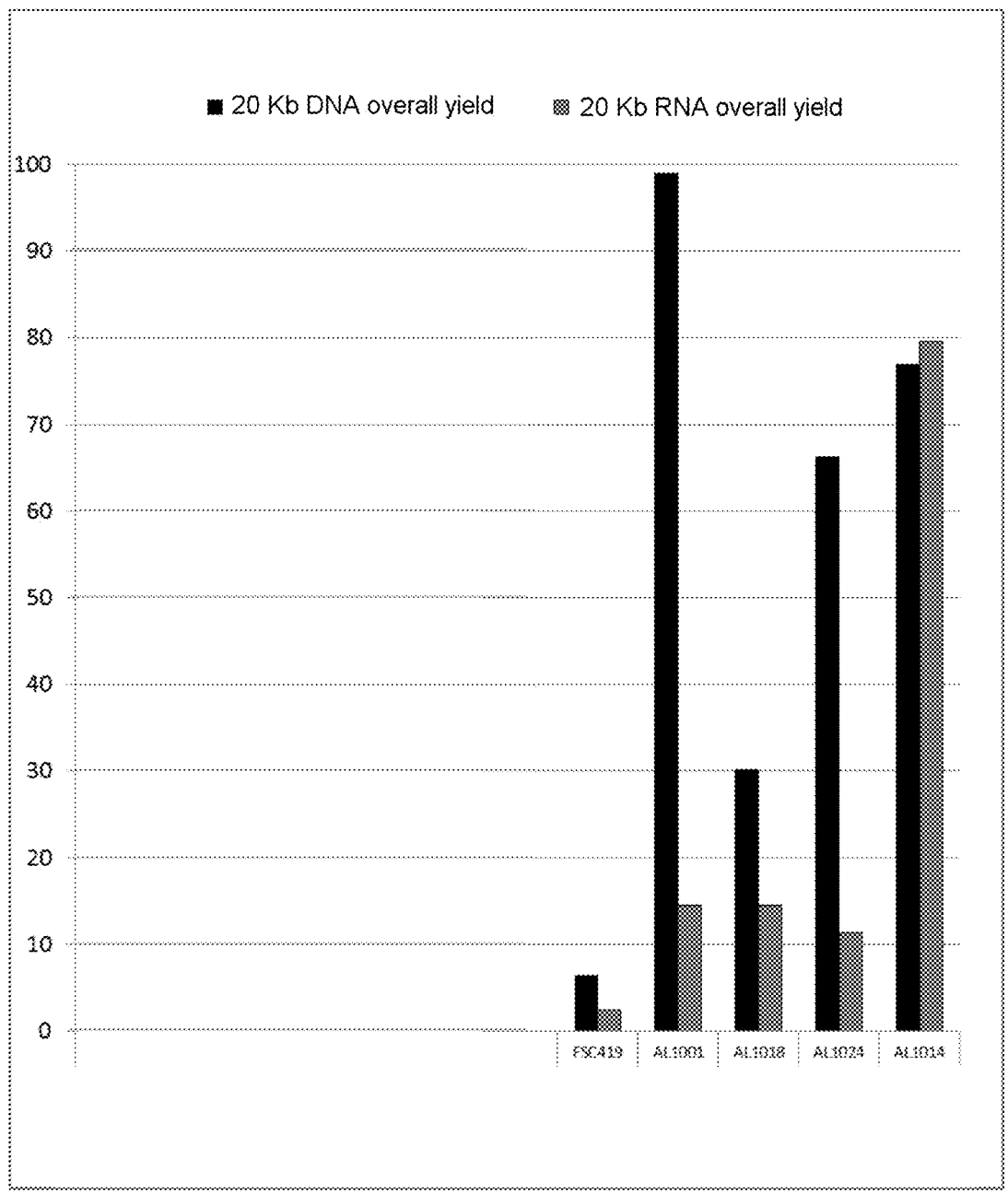
FIG. 6 represents the overall DNA extraction (black) and RNA extraction (gray) yield for magnetite particles covered with inorganic silicate compounds described in FIG. 4.

For greater simplicity, the overall DNA or RNA extraction yield (multiplication of the capture yield by the elution yield as indicated in FIGS. 4 and 5) has been represented in FIG. 6. Thus, the simple coating of the magnetite with inorganic silicate compounds and according to the protocol described above thus constitutes in itself a significant improvement in the nucleic acid extraction properties of the magnetite.

Example 5: DNA and RNA Extraction Yield with Magnetic Particles Coated with Compounds Having an Affinity for Said at Least One Magnetic Compound and/or for Said at Least One Inorganic Silicate Compound Described in Example 2

DNA and RNA extraction experiments were carried out according to the protocol described in example 4 using magnetite particles coated only with compound having an affinity for the at least one magnetic compound and/or for the at least one inorganic silicate compound as synthesized in example 2. FIG. 7 (FIGS. 7A and 7B) describes the capture yield and elution yield measurements thereof. It is demonstrated that, with respect to magnetite, the DNA capture is totally inhibited (FIG. 7A) whereas the RNA capture is not modified but its elution is notably improved (FIG. 7B).

For greater simplicity, the overall DNA or RNA extraction yield (multiplication of the capture yield by the elution yield) has also been represented in FIG. 8, which demonstrates again and still in comparison with magnetite, that the adsorption or capture of compounds having an affinity for said at least one magnetic compound and/or for said at least one inorganic silicate compound on magnetite spectacularly improves the RNA extraction yield, whereas it reduces that of the DNA to nothing.

Example 6: DNA and RNA Extraction Yield with Doubly Coated Magnetic Particles Described in Example 3

DNA and RNA extraction experiments were carried out according to the protocol described in example 4 using magnetic particles doubly coated: 1) with at least one inorganic silicate compound and 2) with at least one compound having an affinity for said at least one magnetic compound and/or for said at least one inorganic silicate compound as synthesized in example 3. Two batches of magnetite were used, one made up of particles of 50 nm and the other of 100 nm. To our great surprise, it is noted that the doubly-coated particles give excellent results (represented in FIGS. 9 and 10) and that they make it possible to extract DNA and RNA much better than those which are coated once (particles of example 1 or 2); the extraction results are much better than the simple addition of the two extraction results with the two-layer complexes of examples 1 and 2, namely the magnetic particles coated with the inorganic silicate compound (example 1) and the particles coated with compounds having an affinity for the inorganic silicate compound and/or for the magnetic compound (example 2).

The DNA capture capacity is substantially maintained compared with the magnetite, but the elution is facilitated. With regard to RNA, the capture capacity is also surprisingly maintained and the elution is very clearly promoted.

In summary and as summarized in FIG. 11, these results are notable and show that the complexes of the invention offer a double performance level: the coating with inorganic silicate compounds makes it possible to retain the benefit of a good DNA extraction yield while at the same time spectacularly increasing the RNA extraction yield following the adsorption of the compounds having an affinity for the inorganic silicate compound and/or for the magnetic compound.

It is worth noting that the coating of the magnetite with a compound having an affinity for the inorganic silicate compound and/or for the magnetic compound, when inorganic silicate compounds have been adsorbed beforehand, does not decrease the DNA extraction yield, whereas this decrease could have been expected since this is the case when only the compounds having an affinity for the inorganic silicate compound and/or for the magnetic compound are adsorbed. Furthermore, it is clearly observed that this double coating provides a synergistic and cooperative effect in the extraction of nucleic acids since it gives better results than the addition of the results obtained with a simple coating, whether it is with inorganic silicate compounds or compounds having an affinity for the inorganic silicate compound and/or for the magnetic compound.

Example 7: Demonstration of the Efficiency of the Doubly-Coated Particles (Three-Layer Complex) for Extraction of the Nucleic Acids Contained in a Blood Sample Using Doubly-Coated Magnetic Particles as Described in Example 3

The easyMAG® nucleic acid extraction automated device (bioMérieux, Marcy l'Etoile, France) was used to test the doubly-coated magnetic particles (three-layer complex) prepared in example 3 with respect to their capacities to extract nucleic acids contained in the white cells of a blood sample. For this, the protocol below was used:

1—200 µl of blood are added to 2 ml of lysis buffer (NucliSENS lysis buffer BMX 200292, bioMérieux, Marcy l'Etoile, France).
2—The sample is subjected to mixing by vortexing for a few seconds and is then left to stand at ambient temperature for 10 minutes.
3—50 µl of magnetic particles at 50 mg/ml in water are added to the solution prepared in example 3, that is to say 2.5 mg, and mixing is carried out immediately by vortexing for 5 seconds.
4—The suspension is incubated at rest for 10 min without stirring, before being transferred into an easyMAG® shuttle wherein the magnetic particles will be washed before eluting the nucleic acids therefrom.
   a. Briefly, the particles are washed in the automated device with a few ml of NucliSENS easyMAG Extraction Buffer 1 (Ref BMX 280130, bioMérieux, Marcy l'Etoile, France)).
   b. The particles are then taken up with a few ml of a 70% ethanol solution.
   c. The elution is finally carried out with 50 µl of NucliSENS easyMAG Extraction Buffer 3 (ref BMX 280132, bioMérieux, Marcy l'Etoile, France) at 70° C. for 5 minutes.
5—The quality of the nucleic acids extracted is then evaluated by measuring the absorption of the eluate between 220 and 750 nm (Nanodrop, Thermo Fischer Scientific, USA).

Example 7A

It is demonstrated on the spectrophotograms below given in FIG. 12 that the quality and the quantity of the nucleic acids extracted increase notably with the three-layer complex (also called particles having a double coating). The magnetite (AB 930, 100 nm) extracts virtually no nucleic acid, the magnetite/Ludox® 6% (AB1760) extracts three times more nucleic acids (260/280 ratio=1.9) with, however, a 260/230 ratio of 1.1 which indicates a salt contamination. The magnetite/Ludox® 6%/PPi 6.8% (AB 1773) extracts once again four times more nucleic acids, but this time of excellent quality since the 260/280 ratio is equal to 2.1 and the 260/230 ratio is equal to 1.7.

Conclusion:

This demonstrates the beneficial and cooperative effect of the three-layer complex on the extraction of nucleic acids from a complex sample such as blood.

Example 7B

Another batch of magnetite (AB 1757, 50 nm) was also coated with pyrophosphate (=KE220) or Ludox® silicate-comprising nanoparticles in an amount of 6% (=AB 1761). The AB1761 product was then coated with 6.8% of PPi (AB 1774) or 6.8% of PPPi (AB 1777). These particles were then used to extract nucleic acids for a blood sample as previously described. The results of FIG. 13 clearly show once again the increase in the nucleic acid capture and elution efficiency with notable 260/280 purities. It can also be noted that the nucleic acid extraction capacity is greater since the particles are smaller. It can also be noted that the magnetite covered only with iron ligands (KE220) gives very poor extraction results, showing even more clearly the cooperative effect of the two types of coating (inorganic silicate compound+compound having an affinity for the at least one magnetic compound and/or the at least one inorganic silicate compound).

Conclusion:

It is clearly shown with this example that there is a synergistic effect of the two coatings on the magnetic particle (three-layer complex according to the invention), this being for the extraction of nucleic acids from blood. Furthermore, it is shown that several types of complexes according to the invention can give very effective results.

Example 7C

Another batch of magnetite (FSC 419, 50 nm) was also coated with Ludox® silicate-comprising nanoparticles in an amount of 6% (=AL 1001). The AL 1001 product was then coated with 6.8% of PPi at 6.8% (AL 1013). These particles were then used to extract nucleic acids from a blood sample as previously described. The results of FIG. 14 clearly show once again the increase in efficiency of these particles according to the invention in the extraction of nucleic acids with notable 260/280 purities. It is again clear that the nucleic acid extraction is potentiated when the complex is three-layer. Indeed, with two-layer complexes (magnetite/PPi or magnetite/Ludox) the extraction is clearly worse. It was not at all foreseeable that the three-layer complex according to the invention would give extraction results even better than the addition of the results obtained for each of the two-layer complexes.

Example 7D

The same batch of magnetite (FSC 419, 50 nm) was also coated with silicate-comprising nanoparticles of bentonite in an amount of 30% (=AL 1014). The AL 1014 product was then coated with 6.8% of PPi (AL 1015). These particles were then used to extract nucleic acids from a blood sample as previously described. The results of FIG. 15 clearly show once again the increase in efficiency of the particles of the invention (three-layer complex) in the extraction of nucleic acids with notable 260/280 purities. It is worth noting that the AL 1014 particles simply covered with bentonite are not efficient for extracting nucleic acids with good purity (260/280 ratio=1.1 only, which indicates a very strong protein contamination as seen on the UV spectrum of FIG. 15).

On the other hand, the coating of these particles (two-layer complex) with pyrophosphate PPi improves the extraction considerably (260/280 ratio=1.7), which once again shows the phenomenon of cooperation and synergy provided by the double coating for forming the three-layer complex of the invention.

Example 8: Amplification and Detection by Real-Time PCR of Cytomegalovirus (CMV) Nucleic Acids Extracted from a Blood Sample Using Three-Layer Complexes According to the Invention (Particles as Described in Example 3)

The easyMAG® nucleic acid extraction automated device (bioMérieux, Marcy l'Etoile, France) and also the CMV R-gene real-time PCR quantification kit (bioMérieux, Marcy l'Etoile, France) were used to test the three-layer complexes according to the invention (doubly-coated magnetic particles prepared in example 3) with regard to their capacities to extract nucleic acids from a blood sample and to the capacity of these extracted nucleic acids to then be amplified. For this, the protocol below was used:

1. 200 µl of blood contaminated by adding a viral culture of cytomegalovirus (CMV produced from CMV Towne, ATCC VR-977) are added to 2 ml of lysis buffer (NucliSENS lysis buffer BMX 200292, bioMérieux, Marcy l'Etoile, France).
2. 10 µl of extraction and inhibition control solution (IC2, contained in the CMV R-Gene® quantification kit (bioMérieux, Marcy l'Etoile, France)) are added to the tube of lysis buffer containing the blood sample.
2'. In parallel in other tubes, control ranges of $10^{e3}$ to $10^{e6}$ copies of CMV are produced.
3. The sample is subjected to mixing by vortexing for a few seconds and is then left to stand at ambient temperature for 10 minutes.
4. 50 µl of magnetic particles at 50 mg/ml in water are added to the solution prepared in example 3, that is to say 2.5 mg, and the mixture is stirred by vortexing immediately for 5 seconds.
5. The suspension is incubated at rest for 10 min without stirring before being transferred into an easyMAG® shuttle wherein the magnetic particles will be washed before eluting the nucleic acids therefrom.
    a. Briefly, the particles are washed in the automated device with a few ml of NucliSENS easyMAG Extraction Buffer 1 (Ref. BMX 280130, bioMérieux, Marcy l'Etoile, France).
    b. The particles are then taken up with a few ml of a 50% ethanol solution.
    c. The elution is finally carried out with 50 µl of NucliSENS easyMAG Extraction Buffer 3 (ref BMX 280132, bioMérieux, Marcy l'Etoile, France) at 70° C. for 5 minutes.
6. The CMV DNA extracted is then amplified and quantified using the protocol and the reagents of the CMV R-Gene® quantification kit on a Bio-Rad CFX-96 thermocycler (Bio-RAD, Hercules, Calif.).

Conclusion:

It is demonstrated, in FIG. 16, that the CMV virus DNA (curves with circles) is amplified with a better sensitivity in the case of the use of the three-layer complex according to the invention (the doubly-coated AL1013 particle (magnetite/Ludox 6% weight/weight/(PPi 6.8%)) compared with the use of the AL 1001 singly-coated particle (magnetite/Ludox 6% weight/weight), respectively with a Cq put forward at 33.7 compared with a Cq of 35.5 in the case of the amplification of the extracted nucleic acids with the particles of magnetite covered only with Ludox® 6%. The exact same thing is true for the amplification of the nucleic acids retained by another complex according to the invention (the doubly-coated particles: AL1015 (magnetite/bentonite 30%/PPi 6.8%)). An amplification detected with much greater sensitivity (Cq=34.8) is also observed, whereas, when using a two-layer complex only, namely the AL 1014 particles (AL1014 magnetite/Bentonite 30%), no amplification is observed.

On each graph, four curves without circles are observed, corresponding to the curves observed with the amplification of the control ranges which contain from $10^{e3}$ to $10^{e6}$ copies of CMV.

The highly advantageous, or even synergistic, effect of the double coating on the magnetic compound for forming the three-layer complexes according to the invention is once again shown.

It should be noted that the magnetite alone under these conditions of use is not responsible for any amplification/detection of the CMV virus.

LITERATURE REFERENCES

Rapid and simple method for purification of nucleic acids, Boom, Journal of Clinical Microbiology, 1990 p 495

Magnetic particles for the separation and purification of Nucleic acids, S. Berensmeier, Applied Microbial Biotechnology 2006 73 495-504

The use of magnetic nanoparticles in the development of new molecular detection systems, I. J. Bruce, Journal of Nanosciences and nanotechnology Optimization of influencing factors of nucleic acid adsorption onto silica-coated magnetic particles: Application to viral nucleic acid extraction from serum, Ning Sun et al., Journal of Chromatography A, 1325 (2014) 31-39

Stability constants of metal-ion complexes, Lars Gunnar SiHen and Arthur Earl Martell, Edition 1971, Chemical Society, G Pourroy, Chem. Comm. 2010 46 985-987

G Pourroy, Chem. Mater., 2008, 20 (18), pp 5869-5875

Isolation of genomic DNA using magnetic cobalt ferrite and silica particles, B. Rittich, J. of Chromatography A, 2004, 43-48

Ferrite supports for the isolation of DNA from complex samples and polymerase chain reaction amplification, D. Horack, J. of Chromatography A, 2005, 93-98

T. Sugimoto and E. Matjevic, Journal of Colloids and Interface Science, 1980, 74, P 227-243

R. Massart, IEEE Trans. Magn. 1981, 17, p 1247-1248

Maity, Journal of Magnetic Materials 321 1256 (2009)

The Influence of Particle Size, Shape and Particle Size Distribution on Properties of Magnetites for the Production of Toners, Journal of Imaging Science and Technology, November/December 2000, vol. 44, no. 6; p. 508-513

W. Stöber, Journal of Colloids and Interface Science 1968, 26, p 62-69

The invention claimed is:

1. A three-layer complex comprising:
   a first layer comprising at least one magnetic compound,
   a second layer partially covering and directly contacting the first layer wherein the second layer is discontinuous and comprises at least one inorganic silicate compound, and
   a third layer at least partially covering and directly contacting both the second layer and the first layer wherein the third layer comprises at least one compound that bonds to the at least one magnetic compound and/or the at least one inorganic silicate compound.

2. The three-layer complex as claimed in claim 1, wherein the at least one magnetic compound is chosen from metals and metal oxides.

3. The three-layer complex as claimed in claim 1, wherein the at least one magnetic compound is chosen from magnetite, maghemite and ferrites.

4. The three-layer complex as claimed in claim 1, wherein the at least one inorganic silicate compound is chosen from magnesium, sodium, potassium, lithium or calcium silicates, talc, aluminosilicates, kaolin, bentonite, silica nanoparticles having a particle size between 0.1 and 20 nm, mesoporous silica nanoparticles, and magnetic nanoparticles covered with silica.

5. The three-layer complex as claimed in claim 4, wherein the at least one inorganic silicate compound is bentonite or silica nanoparticles having a particle size between 0.1 nm and 20 nm.

6. The three-layer complex as claimed in claim 1, wherein the at least one inorganic silicate compound is in particulate form or in a form which is insoluble in an aqueous solvent, an aqueous solvent/organic solvent mixture or an organic solvent.

7. The three-layer complex as claimed in claim 6, wherein the particles or insoluble forms of the inorganic silicate compound have a size of between 0.1 and 20 nm.

8. The three-layer complex as claimed in claim 1, wherein the at least one compound of the third layer is chosen from citric acid and salts thereof, phosphate, pyrophosphate, triphosphate or polyphosphate ions, phosphonic acids, phosphonates, phosphonates or phosphonic acids coupled to organic molecules, compounds of the phosphoric acid family, compounds of the sulfonate family, saponins, Tweens, Tritons, and compounds of the carboxylic acid family.

9. The three-layer complex as claimed in claim 8, wherein the at least one compound of the third layer is a monophosphate, pyrophosphate and/or triphosphate.

10. The three-layer complex as claimed in claim 1, further comprising a solid support under all or part of the first layer.

11. The three-layer complex as claimed in claim 10, wherein the support is a flat support, a hollow support, a round piece, a needle, a membrane, a block, a cone, a tube, a bead, or a particle.

12. The three-layer complex as claimed in claim 1, wherein the complex is in the form of a particle and the third layer is on the outside of the particle.

13. The three-layer complex as claimed in claim 12, wherein the first layer constitutes the core of the particle and has a size of between 2 and 400 nm.

14. A method for preparing at least one three-layer complex as claimed in claim 1, comprising at least the following steps:
   a0) optionally bringing a support into contact with at least one magnetic compound such that the at least one magnetic compound attaches or bonds to the support,
   a) bringing the result of step a0) or at least one magnetic compound into contact with at least one inorganic silicate compound, such that an electrostatic interaction and/or a covalent bond and/or a coordination bond occurs between the at least one magnetic compound and the at least one inorganic silicate compound and such that the layer of the at least one inorganic silicate compound partially covers the layer of the at least one magnetic compound, and
   b) bringing the result of step a) into contact with at least one compound that adheres and positions itself above the layer of the at least one inorganic silicate compound of the two-layer complex, with or without support, and above the magnetic compound where the layer of at least one inorganic silicate compound is discontinuous.

15. A method for preparing at least one three-layer complex as claimed in claim 1, comprising at least the following steps:
   a) bringing at least one magnetic compound into contact with at least one inorganic silicate compound, the inorganic silicate compound already being in particulate form, nanoparticulate form or insoluble form, such that an electrostatic interaction and/or a covalent bond and/or a coordination bond occurs between the at least two compounds and that the particles or insoluble forms partially cover the particle of at least one magnetic compound constituting the core, and
   b) bringing the coated particle obtained at the end of step a) into contact with at least one compound, such that an electrostatic interaction and/or a covalent bond and/or a coordination bond occurs between the at least one compound and the at least one inorganic silicate compound of the two-layer complex obtained at the end of step a) and/or the at least one magnetic compound of the two-layer complex obtained at the end of step a) and that the at least one compound adheres to the surface of the at least one inorganic silicate compound and/or to the core of the final particle.

16. A method comprising purifying microorganisms and/or biomolecules or extracting biomolecules using at least one three-layer complex as claimed in claim 1.

17. A method for detecting and/or quantifying target nucleic acids from a sample that may contain the target nucleic acids, comprising the following steps:
   1. extracting nucleic acids from the sample with the three-layer complex as claimed in claim 1, and
   2. detecting and/or quantifying the target nucleic acids.

18. The method for detecting and/or quantifying the target nucleic acids as claimed in claim 17, wherein, between the nucleic acid extraction step and the nucleic acid detection step, there is a step of eluting the nucleic acids from the three-layer complex and/or a step of amplifying the nucleic acids.

19. A method for lysing microorganisms and/or cells and/or tissues, from a sample, comprising bringing at least one sample into contact with at least one three-layer complex as claimed in claim 1, wherein the at least one inorganic silicate compound and/or the at least one compound of the third layer comprises at least one saponin, Tween, or Triton that enables lysis.

20. The method as claimed in claim 19, wherein the at least one inorganic silicate compound comprises silica nanoparticles having a particle size between 0.1 nm and 20 nm, of which the silica is bonded to at least one saponin and/or the compound of the third layer is chosen from dopamine and derivatives thereof, catechols and derivatives thereof, phosphonic acids, phosphonates, phosphates and compounds of the carboxylic acid family coupled to at least one saponin.

21. A molecular diagnostic kit comprising at least one three-layer complex as claimed in claim 1.

22. The molecular diagnostic kit as claimed in claim 21, further comprising:
   reagents which allow specific amplification of nucleic acids that may be or that are suspected of being contained in a test sample, and/or
   reagents which allow detection and/or quantification of the nucleic acids that may be or that are suspected of being contained in the test sample.

23. The three-layer complex as claimed in claim 1, wherein:
   the at least one inorganic silicate compound is chosen from silica nanoparticles having a particle size between 0.1 and 20 nm, mesoporous silica nanoparticles, and magnetic nanoparticles covered with silica; and
   the silica of the silica nanoparticles, mesoporous silica nanoparticles, or magnetic nanoparticles covered with silica is optionally bonded to an organic or inorganic group.

24. The three-layer complex as claimed in claim 1, wherein a weight-by-weight ratio of the at least one magnetic compound to the at least one compound of the third layer is between 0.1% and 20%.

25. The three-layer complex as claimed in claim 1, wherein a weight-by-weight ratio of the at least one inorganic silicate compound to the at least one magnetic compound is between 0.1% and 60%.

26. The three-layer complex as claimed in claim 1, wherein:
   a weight-by-weight ratio of the at least one magnetic compound to the at least one compound of the third layer is between 0.1% and 20%; and a weight-by-weight ratio of the at least one inorganic silicate compound to the at least one magnetic compound is between 0.1% and 60%.

* * * * *